(12) United States Patent
Diresta et al.

(10) Patent No.: US 7,435,587 B2
(45) Date of Patent: Oct. 14, 2008

(54) APPARATUS FOR GROWING CELLS UNDER VARIABLE HYDROSTATIC PRESSURES

(75) Inventors: Gene R. Diresta, Pleasantville, NY (US); John H. Healey, New York, NY (US); Robert Schwar, Forestburgh, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 355 days.

(21) Appl. No.: 11/018,094

(22) Filed: Dec. 20, 2004

(65) Prior Publication Data

US 2005/0101008 A1 May 12, 2005

Related U.S. Application Data

(63) Continuation-in-part of application No. 10/378,585, filed on Mar. 3, 2003.

(60) Provisional application No. 60/360,976, filed on Mar. 1, 2002.

(51) Int. Cl.
*C12N 5/02* (2006.01)

(52) U.S. Cl. .............. 435/325; 435/283.1; 435/289.1; 435/304.1; 435/305.1

(58) Field of Classification Search .............. 435/325, 435/283.1, 289.1, 304.1, 305.1
See application file for complete search history.

(56) References Cited

U.S. PATENT DOCUMENTS 4,833,089 A 5/1989 Kojima et al.
4,851,354 A 7/1989 Winston et al.

FOREIGN PATENT DOCUMENTS

EP 0 707 186 A1 4/1996

OTHER PUBLICATIONS

Ute Hansen, Michael Schumke, Christian Domm, Niki Ioannidis, Joachim Hassenpflug, Thorsten Gehrke, Bodo Kurz. "Combination of reduced oxygen tension and intermittent hydrostatic pressure: a useful tool in articular cartilage tissue engineering," Journal of Biomechanics 34, 941-949 (2001).
Cornelia Hasel, Susanne Durr, Silke Bruderlein, Ingo Melzner, Peter Moller. "A cell-culture system for long-term maintenance of elevated hydrostatic pressure with the option of additional tension," Journal of Biomechanics 35, 579-584 (2002).
Jenneke Klein-Nulend, Jan Roelofsen, Cornelis M. Semeins, Antonius L.J.J. Bronckers, and Elisabeth H. Burger. "Mechanical Stimulation of Osteopontin mRNA Expression and Synthesis in Bone Cell Cultures," Journal of Cellular Physiology 170, 174-181 (1997).
Thomas D. Brown. "Techniques for mechanical stimulation of cells in vitro: a review," Journal of Biomechanics 33, 3-14 (2000).
Salwen SA, Szarowski DH, Turner JN, Bizios R. "Three-dimensional changes of the cytoskeleton of vascular endothelial cells exposed to sustained hydrostatic pressure," Medical and Biological Engineering and Computing, 36(4), 520-527 (1998).
Nagatomi J, Arulanandam BP, Metzger DW, Meuniera, Bizios R. "Frequency- and duration-dependent effects of cyclic pressure on select bone cell functions," Tissue Engineering, 7(6), 717-728(2.
Mitchell SB, Sanders JE, Garbini JL, Schuessler PK. "A device to apply user-specific strains to biomaterials in culture," IEEE Trans Biomed Eng 48(2), 268-273, (2001).
Ozawa H, Imamura K, Abe E, Takahashi N, Hiraide T, Shibasaki Y, Fukuhara T, Suda T. "Effect of a continuously applied compressive pressure on mouse osteoblast-like cells (MC3T3-E1) in vitro," Journal of Cellular Physiology, 142(1), 177-185 (1990).
Saito S, Ngan P, Rosol T, Saito M, Shimizu H, Shinjo N, Shanfeld J, Davidovitch Z. "Involvement of PGE synthesis in the effect of intermittent pressure and Interleukin-1—on bone resorption," J Dent Res Jan, 70(1), 27-33 (1990).
Takano-Yamamoto T, Soma S, Nakagawa K, Kobayashi Y, Kawakami M, Sakuda M. "Comparison of the effects of hydrostatic compressive force on glycosaminoglycan synthesis and proliferation in rabbit chondrocytes from mandibular condylar cartilage, nasal septum, and spheno-occipital synchondrosis in vitro," Am J Orthod Dentofacial Orthop, 99(5), 448-55 (1991).
Koyama S, Miwa T, Sato T, Aizawa M. "Optical chamber system designed for microscopic observation of living cells under extremely high hydrostatic pressure," Extremophiles Dec., 5(6), 409-15, (2001).
Kaarniranta K, Elo MA, Sironen RK, Karjalainen HM, Helminen HJ, Lammi MJ. "Stress responses of mammalian cells to high hydrostatic pressure," Biorheology 40, 87-92 (2003).
Tezel J G, Wax MB. "Increased production of tumor necrosis factor-alpha by glial cells exposed to simulated ischemia or elevated hydrostatic pressure induces apoptosis in cocultured retinal ganglion cells," The Journal of Neuroscience. 20(23), 8693-700, Dec. 1, 2000.
Nerucci F, Fioravanti A, Cicero MR, Marcolongo K, SpiHaset C, Durr S, Bruderlein S, Melzner I, Moller P. "Preparation of a pressurization system to study the effect off a hydrostatic pressure on chondrocyte cultures," In Vitro Cellular & Developmental Biology. Animal 34:9-10, Jan. 1998.

(Continued)

*Primary Examiner*—L Blaine Lankford
*Assistant Examiner*—Susan E. Fernandez
(74) *Attorney, Agent, or Firm*—Law Offices of Albert Wai-Kit Chan, PLLC

(57) ABSTRACT

This invention provides an apparatus for growing cells under static or dynamic physiological pressure which contains a cell culture cassette having a cassette frame; two side walls secured to each side of the cassette frame to form a cell growing chamber, and at least one side wall comprises a cell growth surface. The apparatus also contains a means for adjusting fluid pressure or flow, for providing culture media or cell culture, or for sampling cell culture or culture media within the cell growing chamber. The apparatus further contains an adapter which contains two side assemblies where each side assembly includes a frame with a rigid support that fits over the cell culture cassette. The side assemblies joined by a hinge at one end and positioned over the two side walls of the cell culture cassette. The apparatus further contains a means to secure the two side assemblies over the two side walls of the cell culture cassette.

17 Claims, 18 Drawing Sheets

OTHER PUBLICATIONS

Figure 1:
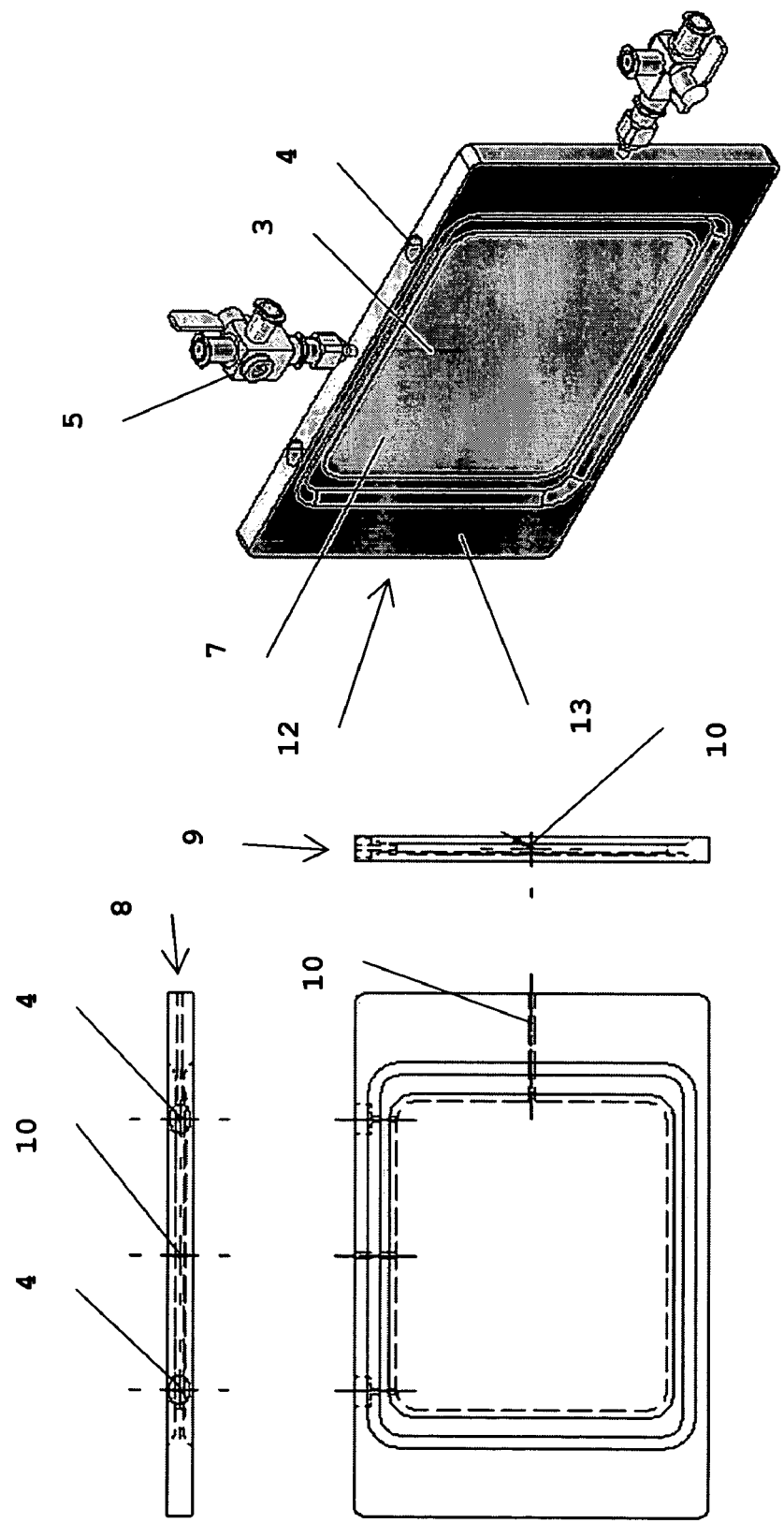

Wax MB, Tezet G, Kobayashi S. Hernandez MR. "Responses of different cell lines from ocular tissues to elevated hydrostatic pressure," Br J Ophthalmol 84, 423-428 (2000).

Saris DB, Sanyal A, An KN, Fitzsimmons JS, O'Driscoll SW. "Periosteum responds to dynamic fluid pressure by proliferating in vitro," Journal of Orthopaedic Research 17(5), 668-677 (1999).

Suh JK, Baek GH, Aroen A, Malin CM, Niyibizi C, Evans CH, Westerhausen-Larson A. "Intermittent sub-ambient interstitial hydrostatic pressure as a potential mechanical stimulator for chondrocyte metabolism," Osteoarthritis Cartilag, 7(I):71-80 (1999).

Carver SE, Heath CA. "Semi-continuous perfusion system for delivering intermittent physiological pressure to regenerating cartilage," Tissue Engineering 5(I), 1-11 (1999).

Hartig M, Ulrich J, Haas-Peter Wiesmann. "Capacitively coupled electric fields accelerate proliferation of osteoblast-like primary cells and increase bone extracellular matrix formation in vitro," Eur. Biophys J 29, 499-506 (2000).

Brighton CT, Wang W, Seldes R, Zhang G. and Pollack S. "Signal Transduction in Electrically Stimulated Bone Cells," JBJS 83 A (10): 1514-23, (2001).

Hiroyuki Ozawa, Etsuko Abe, Yoshinobu Shibasaki, Tatsuo Fukuhara, and Tatsuo Suda. "Electric Fields Stimulate DNA Synthesis,of Mouse Osteoblast-Like Cells (MC3T3-E1) by a Mechanism Involving Calcium Ions," Journal of Cellular Physiology 138:477-483 (1989).

Peter F. Armstrong, Carl T. Brighton, and Andrew M. Star. "Capacitively Coupled Electrical Stimulation of Bovine Growth Plate Chondrocytes Grown in Pellet Form," Journal Orthopaedic Research 6:265-271, (1988).

Gunter Fuhr, Henning Glasser, Torsten Muller, Thomas Schnelle. "Cell manipulation and cultivation under a.c. electric field influence in highly conductive culture media," Biochimica et Biophysica Acta 1201, 353-360 (1994).

Carl T. Brighton, M.D., Ph.D., Enyi Okereke, M.D., Solomon R. Pollack, Ph.D., Charles C. Clark, Ph.D., "In Vitro Bone-Cell Response to a Capacitively Coupled Electrical Field," Clinical Orthopaedics and Related Research. No. 285, 255-62 (1992).

Korenstein R. Somjen D. Fischler H. Binderman I. "Capacitative pulsed electric stimulation of bone cells induction of cyclic amp changes and DNA synthesis," Biochimica et Biophysica Acta. 803(4):302-7 (1984).

Karen M. Haberstroh, Martin Kaefer, Natacha DePaola, Sarah A. Frommer, Rena Bizios. A Novel In-Vitro System for the Simultaneous Exposure of Bladder Smooth Muscle Cells to Mechanical Strain and Sustained Hydrostatic Pressure, Journal of Biomechanical Engineering 124, 208-213 (2002).

U.S. Appl. No. 10/378,585, filed Mar. 3, 2003, DiResta et al.

U.S. Office Action for DiResta, et al., U.S. Appl. No. 10/378,585, filed Mar. 3, 2003, dated Jan. 13, 2006.

U.S. Office Action for DiResta, et al., U.S. Appl. No. 10/378,585, filed Mar. 3, 2003, dated Jul. 5, 2006.

U.S. Office Action for DiResta, et al., U.S. Appl. No. 10/378,585, filed Mar. 3, 2003, dated Mar. 26, 2007.

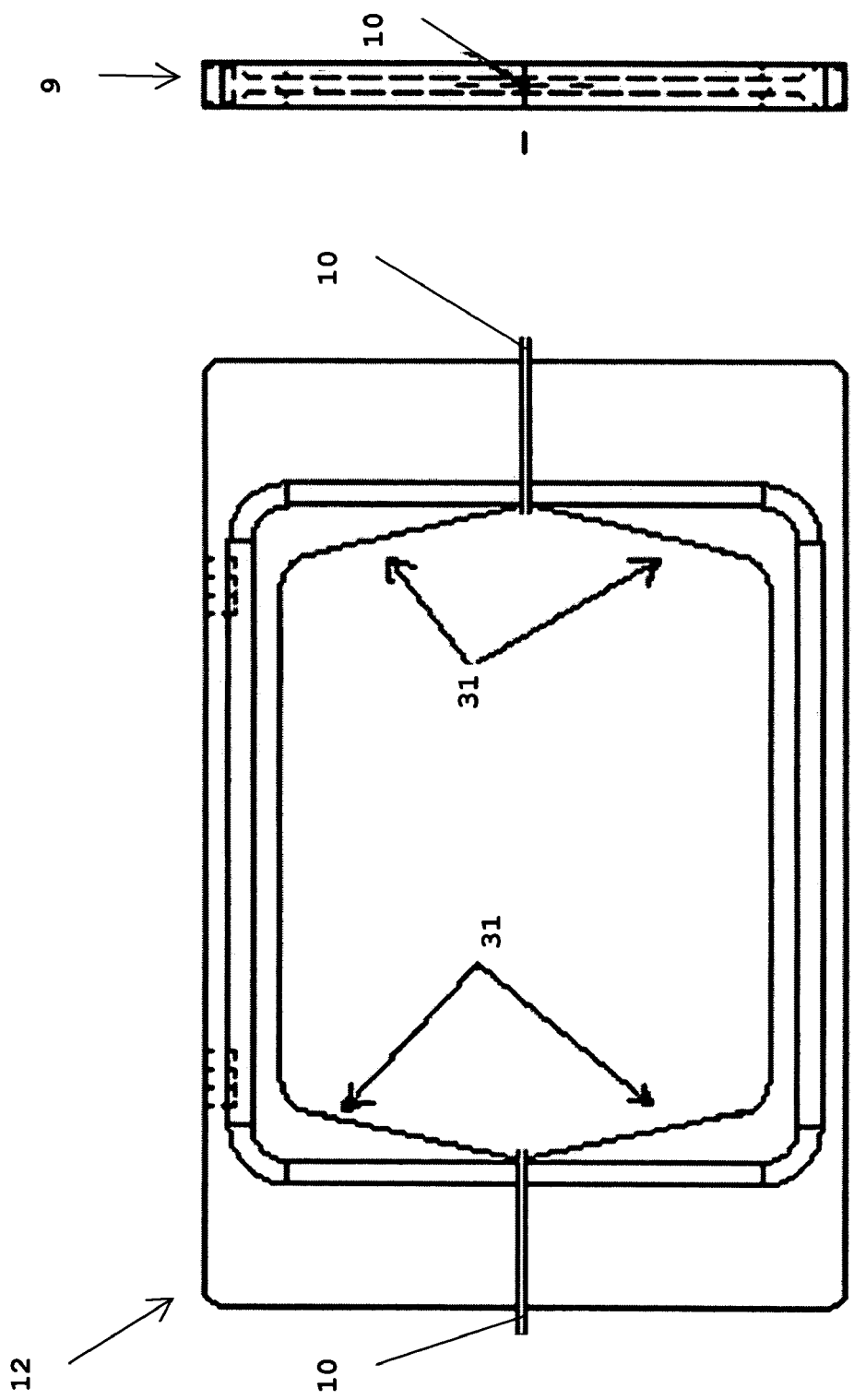

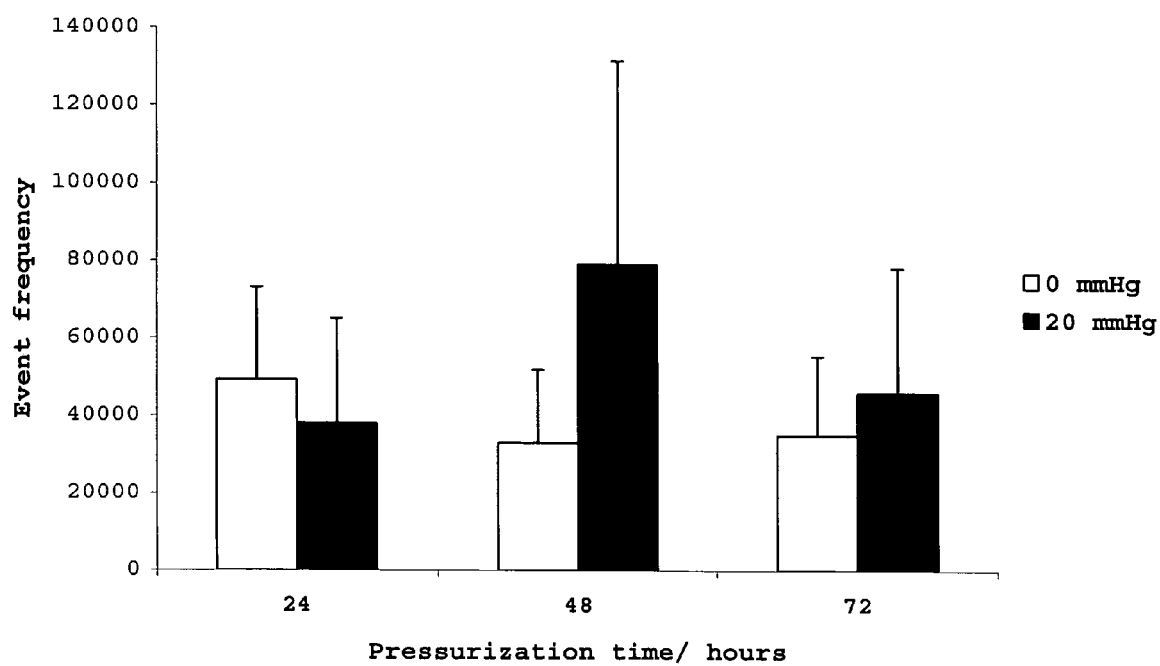

Figure 12
A
Doxorubicin cytotoxicity with depressurized cells
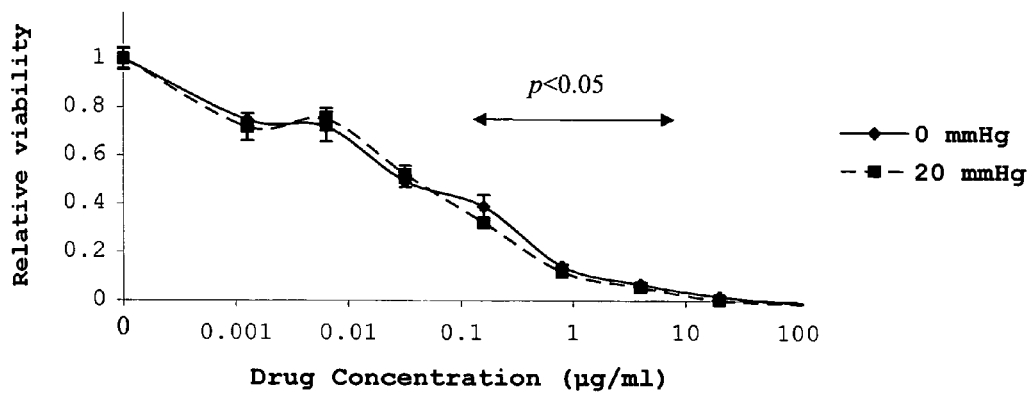
B
Cisplatin cytotoxicity with depressurized cells
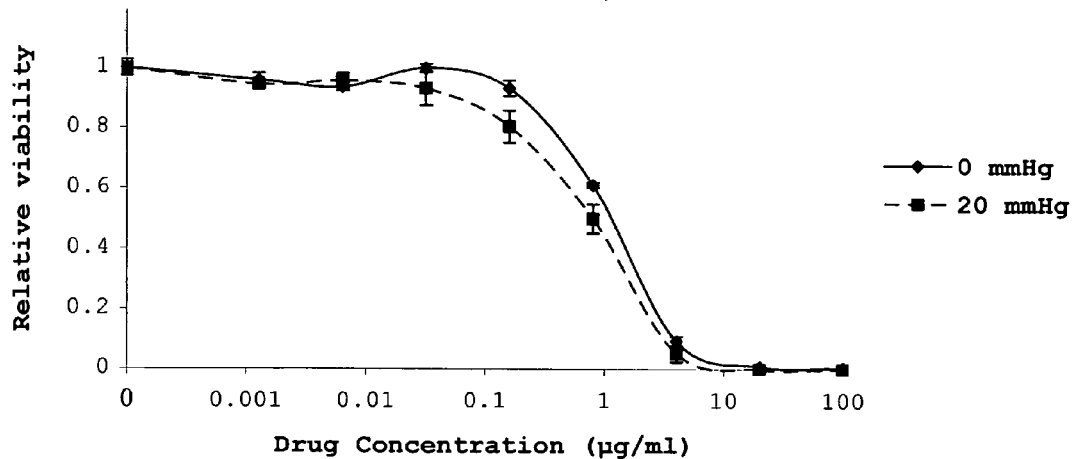

Figure 13
A
Doxorubicin sensitivity of HOS under pressure
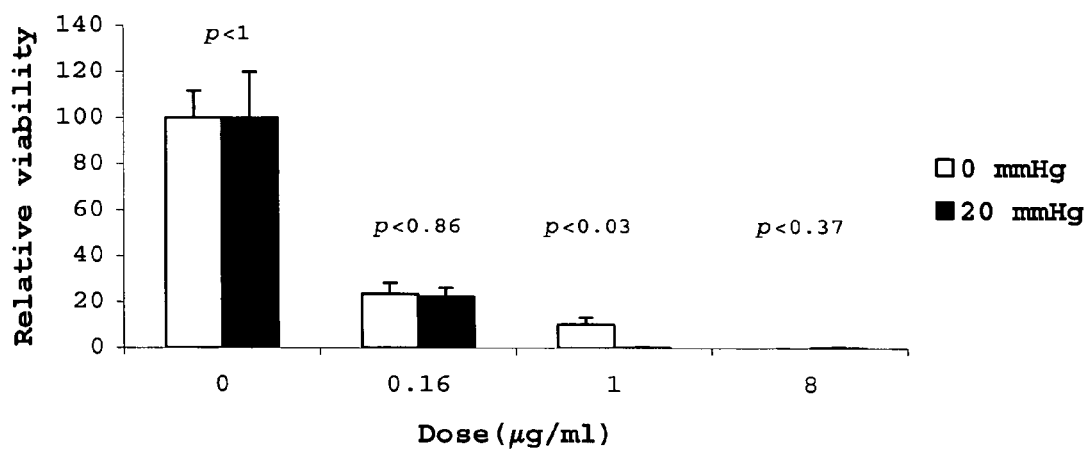
B
Cisplatin sensitivity of HOS under pressure
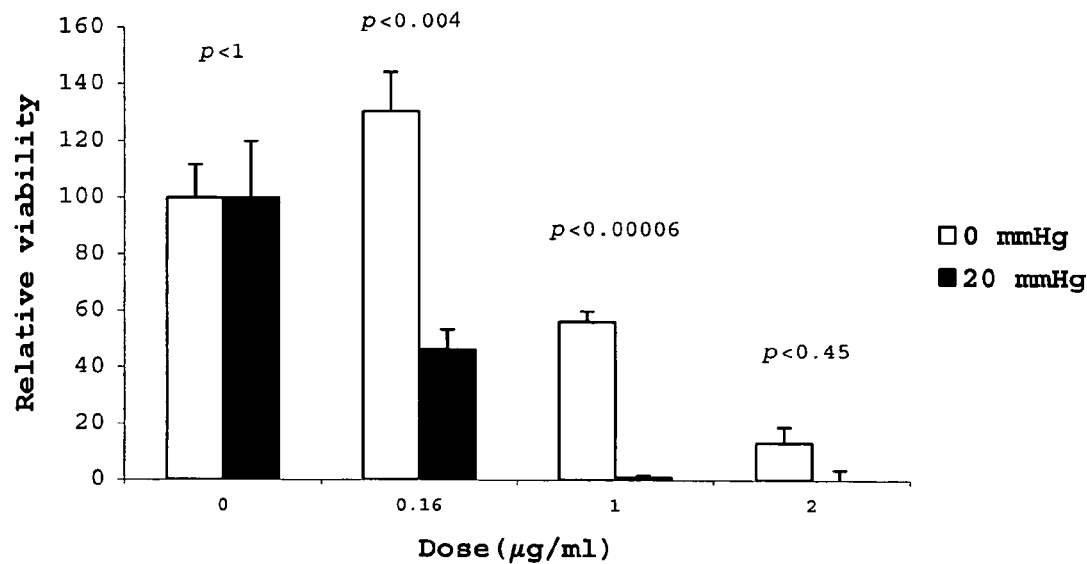

US 7,435,587 B2

APPARATUS FOR GROWING CELLS UNDER VARIABLE HYDROSTATIC PRESSURES

The application herein is a continuation-in-part of U.S. Ser. No. 10/378,585, filed Mar. 3, 2003, which claims benefit of U.S. Ser. No. 60/360,976, filed Mar. 1, 2002, the contents of these applications are incorporated in their entireties by reference here into this application.

Various references are referred to throughout this application. Disclosures of these publications in their entireties are hereby incorporated by reference into this application to more fully describe the state of the art to which this invention pertains.

The invention disclosed herein was supported in part by National Cancer Institute Grant No. 78494. Accordingly, the United States Government may have certain rights in this invention.

BACKGROUND OF THE INVENTION

Laboratory cell culture is a biological technique used to grow cells, bacteria, etc. under sterile conditions. It is typically performed using a Petri dish or culture bottle filled with a small volume of nutrient media and placed within a temperature controlled, humidified incubator. The cells within the dish or bottle exchange gases with the ambient gas atmosphere within the incubator. It is a two dimensional (2-D) technology because cells typically grow on the bottom of the container or on the surface of the media or plastic.

Two dimensional cell culture is a suitable approach for most cells and bacteria, and is used for growing solid tumor cells. The approach, however, does not simulate the in vivo conditions experienced by growing solid tumor cells because these cells grow under conditions of elevated interstitial fluid pressures. These pressures are typically equivalent to the pressures within the arterioles that are feeding the tumor's capillary network. In bone tumors, pressures exceeding 50 mmHg (gauge) have been observed. Further, the elevated pressures alter the genetic expressions of tumor cells. Thus when studying the behavior of solid tumor cells, i.e. their response to chemotherapeutic agents, cells grown using the traditional 2-D approach may not reflect the behavior of their in vivo counterparts because of the major differences between the growth conditions.

Attempts to culture cells under elevated pressure environments have utilized elevated gas pressure within the Petri dish or culture bottle incubator to achieve the desired pressure. However, the problem with this approach is the growth media's gas content is equilibrated to that of the imposed incubator gas pressure in accordance with Henry's Law. The dissolved gas content is thus higher than physiologic levels. While tumor interstitial fluid pressures are elevated, the gas content of the fluid is only equilibrated to one atmosphere because that is the pressure within the lung, the organ primarily responsible for gas equilibration.

The cassette is a new approach to cell culture introduced by BioCrystal, Ltd. It consists of a thin plastic case with two gas permeable membranes and two rubber infusion ports. The cassette permits cell culture under conventional growth conditions in a fully enclosed chamber with rapid gas exchange and cell harvest. Its design, however, is not capable of tolerating the elevated pressures needed to culture tumor cells. Pressurization of the cassette media results in bulging of the membrane sides. The effects of bulging include changing the media volume and membrane thickness as a function of pressure, increasing the membranes' susceptibility to rupture, and increasing the diffusion path for gas exchange within the media.

SUMMARY OF INVENTION

This invention provides an apparatus for growing cells in a cell culture cassette having a matrix for cell growth under pressure comprising two side assemblies which include a frame with a rigid support that fits over the cell culture cassette, with said assemblies positioned on either side of the cassette over the solid support sides, and a means to secure the sides of the cassette.

This invention provides a method of growing cells in 2-D and 3-D mode under static or variable pressure comprising steps of: (a) seeding said cells in the fluid growth media within cassette; (b) placing the cassette of step (a) into the above-described apparatus; and (c) applying static or dynamic hydrodynamic pressure via the side or top port(s) on the cassette.

This invention provides a composition comprising cells grown by the above method. This invention also provides a composition comprising the extract of cells grown by the above method.

This invention provides a method for identifying an agent capable of inhibiting tumor cell growth comprising steps of: (a) contacting said agent at an appropriate concentration with tumor cells under pressure; and (b) examining the tumor cells to determine whether the growth of tumor cells is inhibited.

This invention provides a method for determining effective amount of an agent capable of inhibiting tumor cell growth comprising steps of: (a) contacting said agent at different amounts with tumor cells under pressure; (b) examining the tumor cells to determine whether the growth of tumor cells is inhibited; and (c) determining the amount which causes tumor cell inhibition.

This invention provides a method for screening compounds capable of inhibiting tumor cells growth comprising steps of: (a) contacting said compounds with tumor cells under pressure; and (b) identifying the compound which inhibits the growth of the tumor cell.

DETAILED DESCRIPTION OF THE FIGURES

FIG. 1. Cell Culture Cassette Showing Pressurization Port. This figure is the modified cell culture cassette 12 showing side port valve 5 machined along either of the short sides 9. Valves 5 can also be placed on long side 8 of the cassette. A valve 5 can be placed into the center of the long side in between the rubber ports 4 of cassette to facilitate pressurization of the cassette. The valve is normally closed unless pressurization is performed. It is intended for continuous pressurization. The cassette is a chamber with two gas-permeable membrane 7 growth surfaces. Cells placed within the chamber rapidly adhere to the membrane and form protein bonds with the growth surfaces variably over a 24-hour period. Gas exchange with the incubator's atmosphere occurs directly through the membrane. Reference numeral 10 shows locations of a machined port used to position a valve or to accept a valve. Other locations on the short or long sides are also possible to a) facilitate flow-through cell culture, b) introduce fluid shear pressure profiles or turbulence to cells attached to membranes in addition to pressurization.

Figure 2:
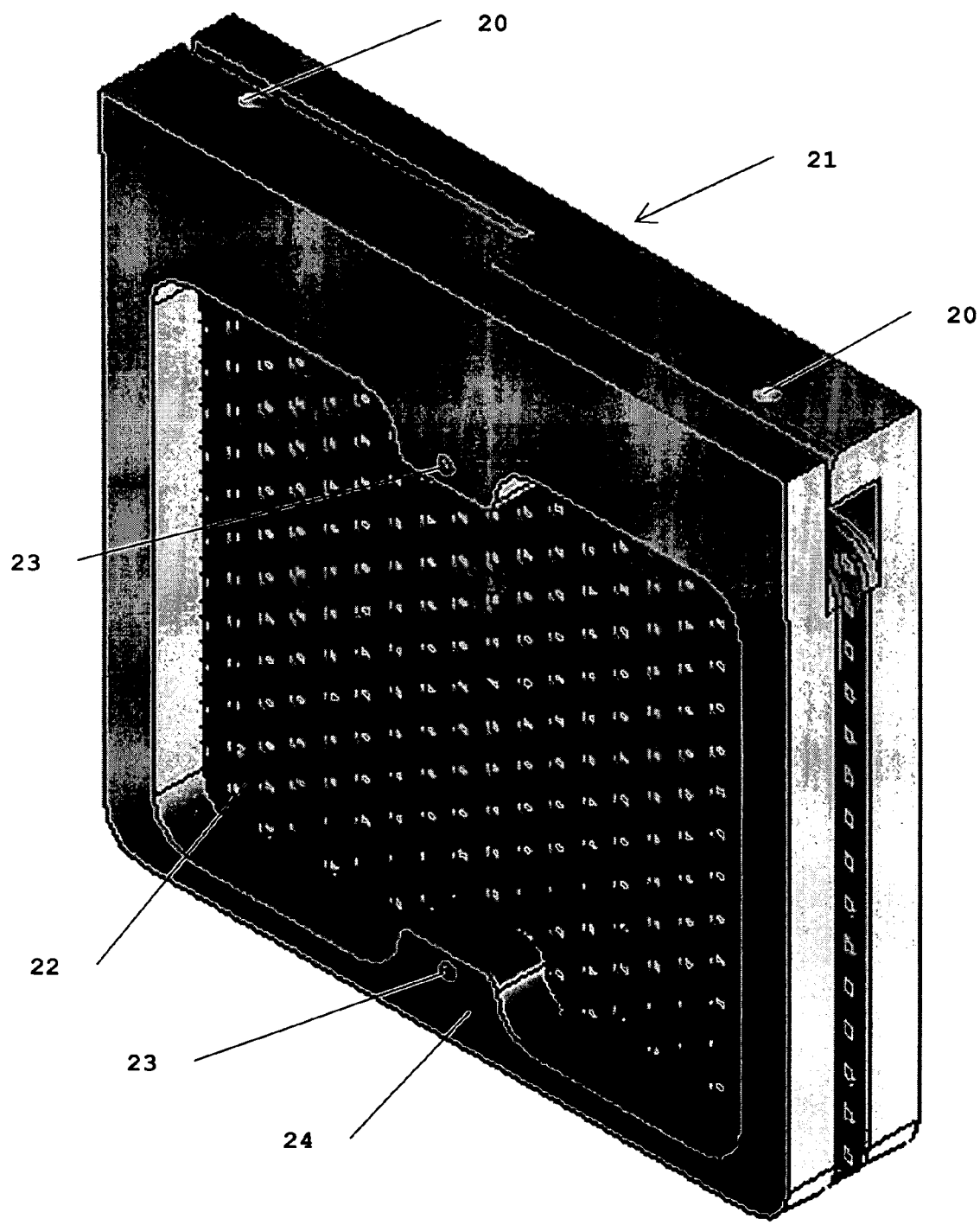

FIG. 2. Cell Culture Cassette High Pressure Adapter. This figure shows the high pressure adapter (HPA) 21. The HPA is composed of two mirror images sections 24 that join in a hinge at the top. The sections are made from a machineable, heat- and moisture-resistant plastic. This plastic may also be autoclavable. The hinge enables the HPA to fold over the cell culture cassette over the side that contains the two rubber access ports 20. The HPA closure ends with contact to the cassette's membrane frame. The stainless steel mesh 22 covers the exposed membrane window without making contact with the membrane until the cassette is pressurized. Pressurization is accomplished using media injected into the cassette via a needle 3 into one of the rubber ports or via the pressure port of the modified cell culture cassette. The pressure is observed using a gauge on the other port or via a three-way valve. The HPA is held in place by inserting the cassette with the HPA into the HPA multi-cassette holder or with a slide closure. The side port is used to control pressurization. Two fasteners 23 are used to hold the mesh to the frame. When the HPA is used to apply an electric field, the fasteners are metal. One fastener on each side of the adapter can serve as the contact point for the electric field electrodes.

FIG. 3. Modified Flow-Through Cell Culture Cassette Showing Baffles. The cassette design will include at least two fluid entry luer valve fittings to facilitate flow through capability at elevated hydrostatic pressures without leakage. Baffles 31 placed at the two short sides within the cassette direct flow to avoid dead zones. The baffles reduce turbulence and insure laminar flow when the cassette is used in flow-through mode. The input or output ports 10 are located on the opposite sides of modified cell culture cassette. Alternative baffle designs, port locations, diameter and the number of ports are possible to skilled users to create alternative flow profiles and multi-input multi-output designs.

Figure 4A:
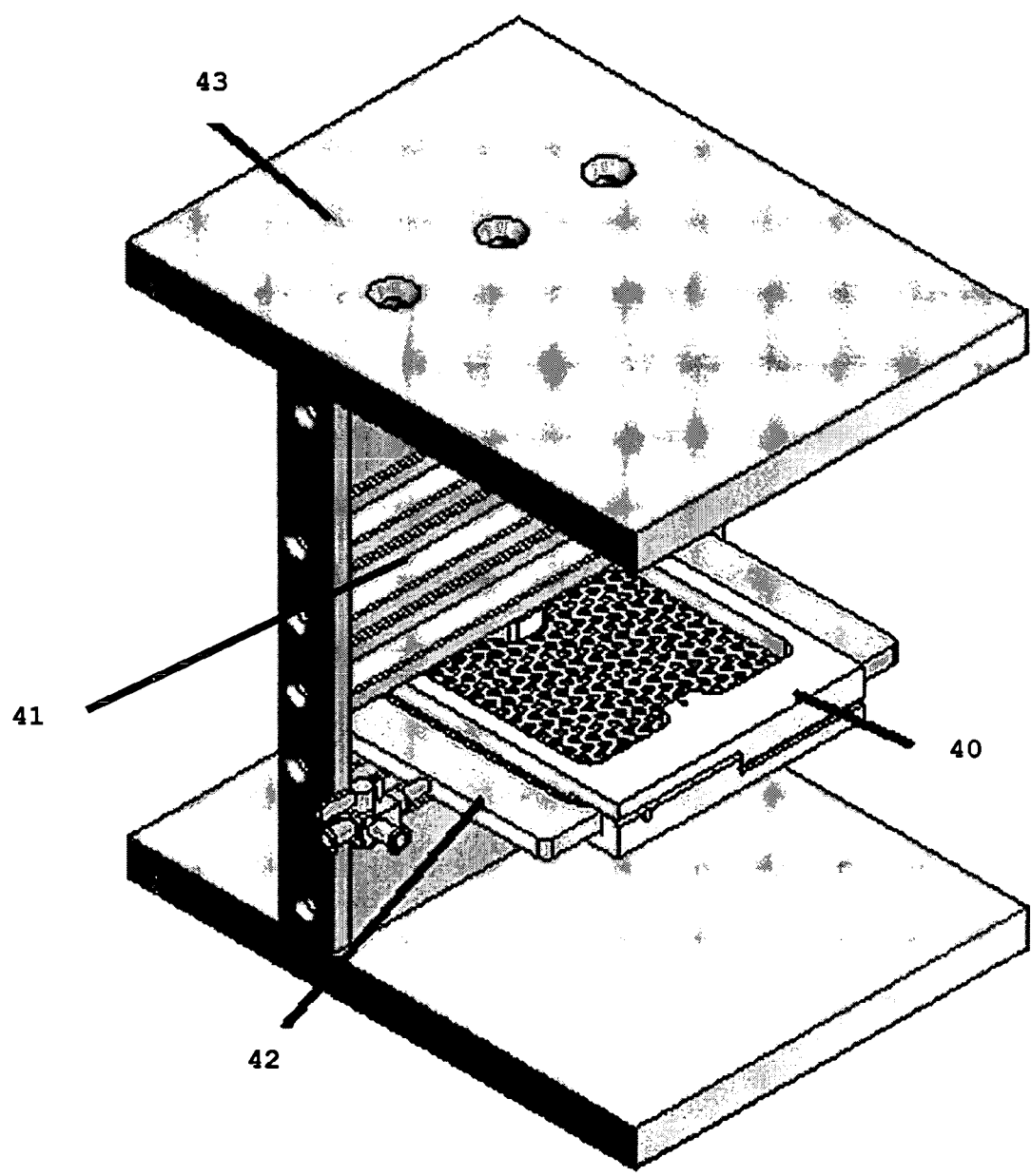

FIG. 4A. Detail of the HPA multi-cassette holder. The holder 43 is a plastic container dimensioned to hold up to six cassettes with HPAs in place. The cassette-HPA assemblies are inserted into spaced grooves 41 at the base of the multi-cassette holder. The size of the multi-cassette holder can be fabricated to hold any number of assemblies. Reference numeral 40 shows the high pressure adapter, and reference numeral 42 shows modified cell culture cassette with pressurization fitting. The device positioned as shown creates a pressure gradient among the cassettes within the holder, i.e. cassettes placed at the top will have a lower pressure than those at the bottom in accordance with hydrostatic pressure position between the top of the holder to the bottom when holder is positioned with the cassettes pointing up, i.e., oriented in a vertical position, all cassettes receive the same hydrostatic pressure.

Figure 4B:
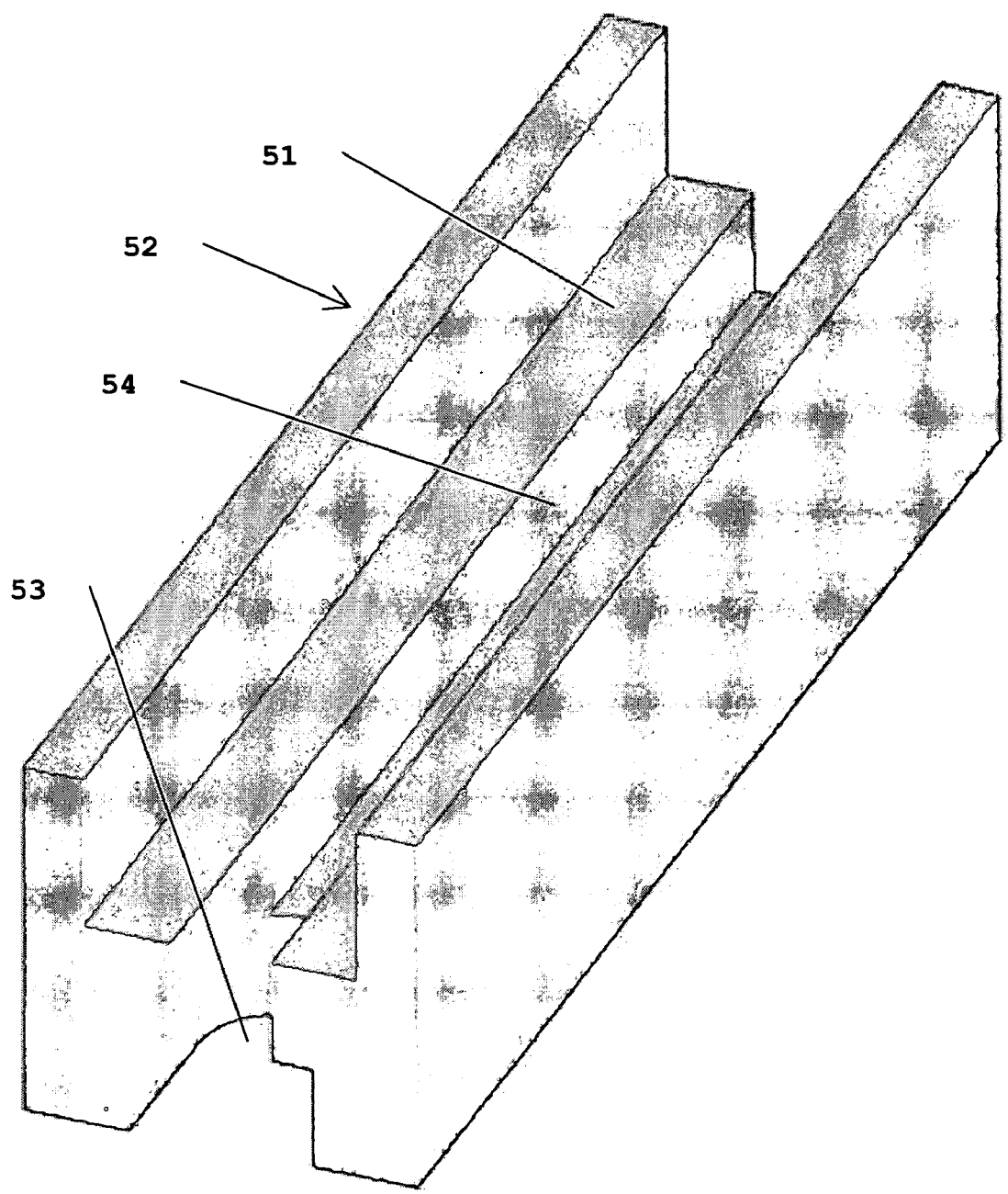

FIG. 4B. Slide Closure 52. The figure shows a device that is used to secure the HPA around the cassette. It has a channel pattern that accepts the cassette 54 and a channel pattern that accepts HPA sides 51 to secure the HPA to the cassette. The channel runs the length of the device with a slot 53 on one end to accommodate a three-way value positioned in one of the cassette's rubber ports. It slides over the top end of the HPA and is used as an alternative to the multi-cassette holder.

Figure 5:
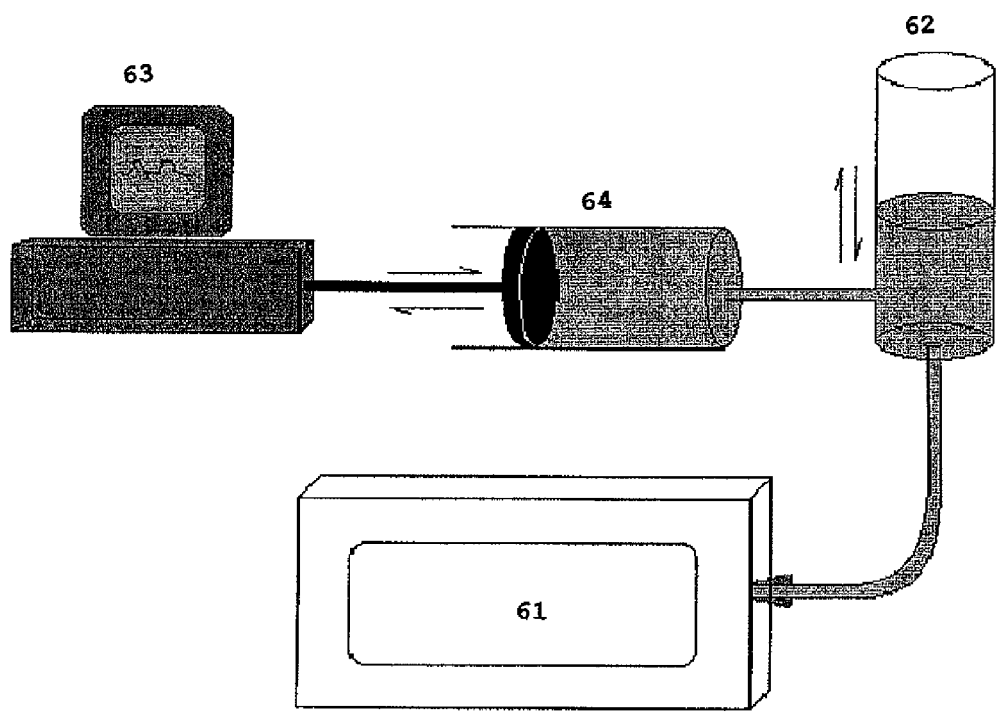

FIG. 5. Method for generating variable hydrostatic pressure within the cassette. 1) The valve is connected to side port of the pressurized cell culture cassette 61, e.g. through luer connection. 2) The sterile fluid reservoir 62 is prefilled with sterile fluid to the mean desired hydrostatic pressure. 3) The computer regulator 63 is turned on. 4) The computer algorithm generates piston motion in the bi-directional computer-controlled syringe pump 64 to adjust the level within the fluid reservoir such that the level corresponds to the maximum and minimum hydrostatic pressure desired within the cassette. The intent is to simulate the variable hydrostatic pressure profile the heart generates.

Figure 6:
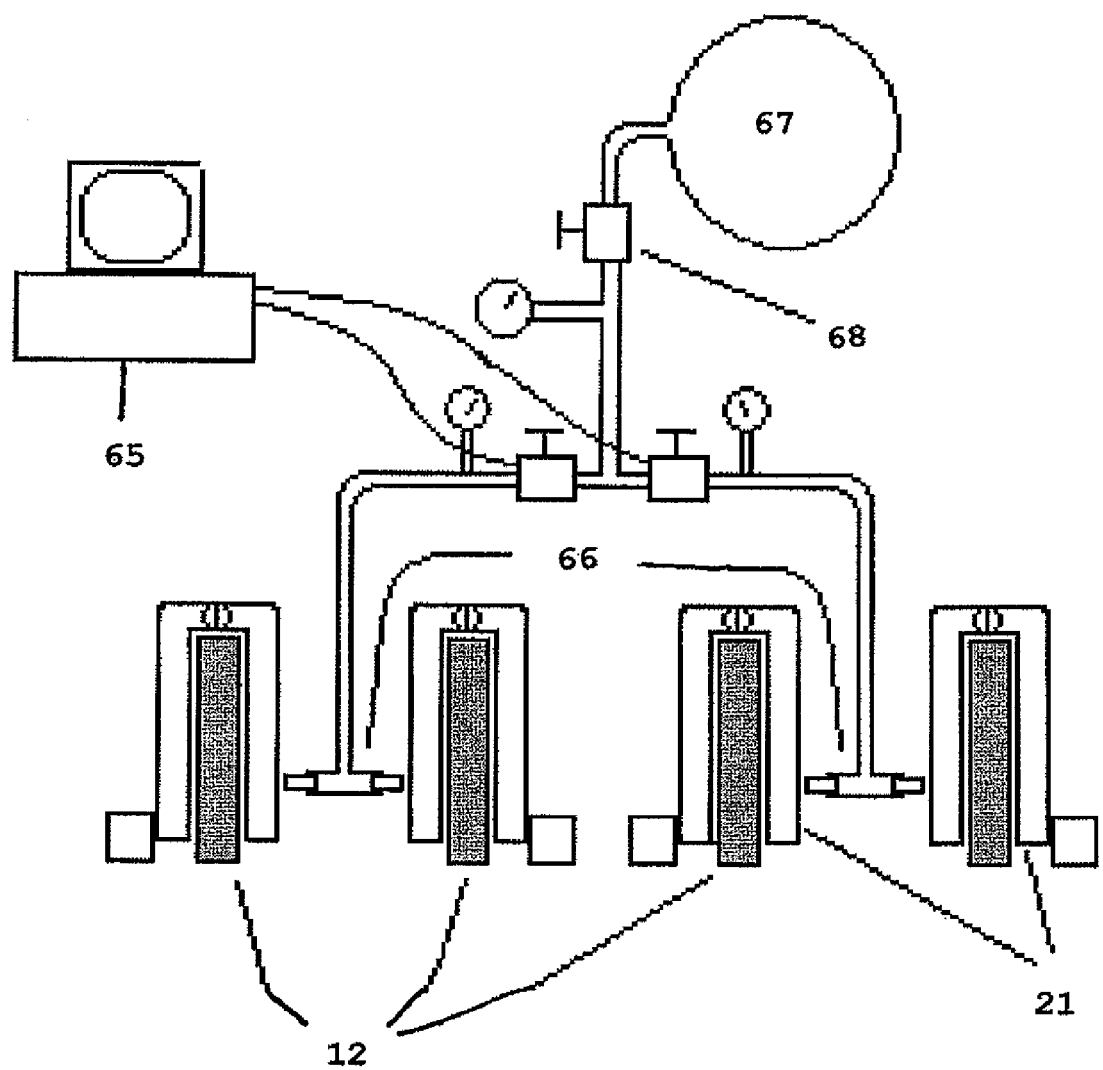

FIG. 6. Alternative Method of Varying Pressure within Cassette with High Pressure Adapter. The figure shows four cassettes 12. This approach takes advantage of the metal screen with an external device which causes the fluid within the cassette to compress and subsequently pressure to increase. The types of external devices that could be used to push against the screen include fluid filled piston 66 applying pressure to the steel sides of the HPA 21 of four cassettes 12. The fluid used is gas, i.e. air. A computer 65 controls the valves and timing. Alternatively electronically driven solenoids can provide the piston motion. 67: gas tank; 68: regulator valves.

Figure 7A:
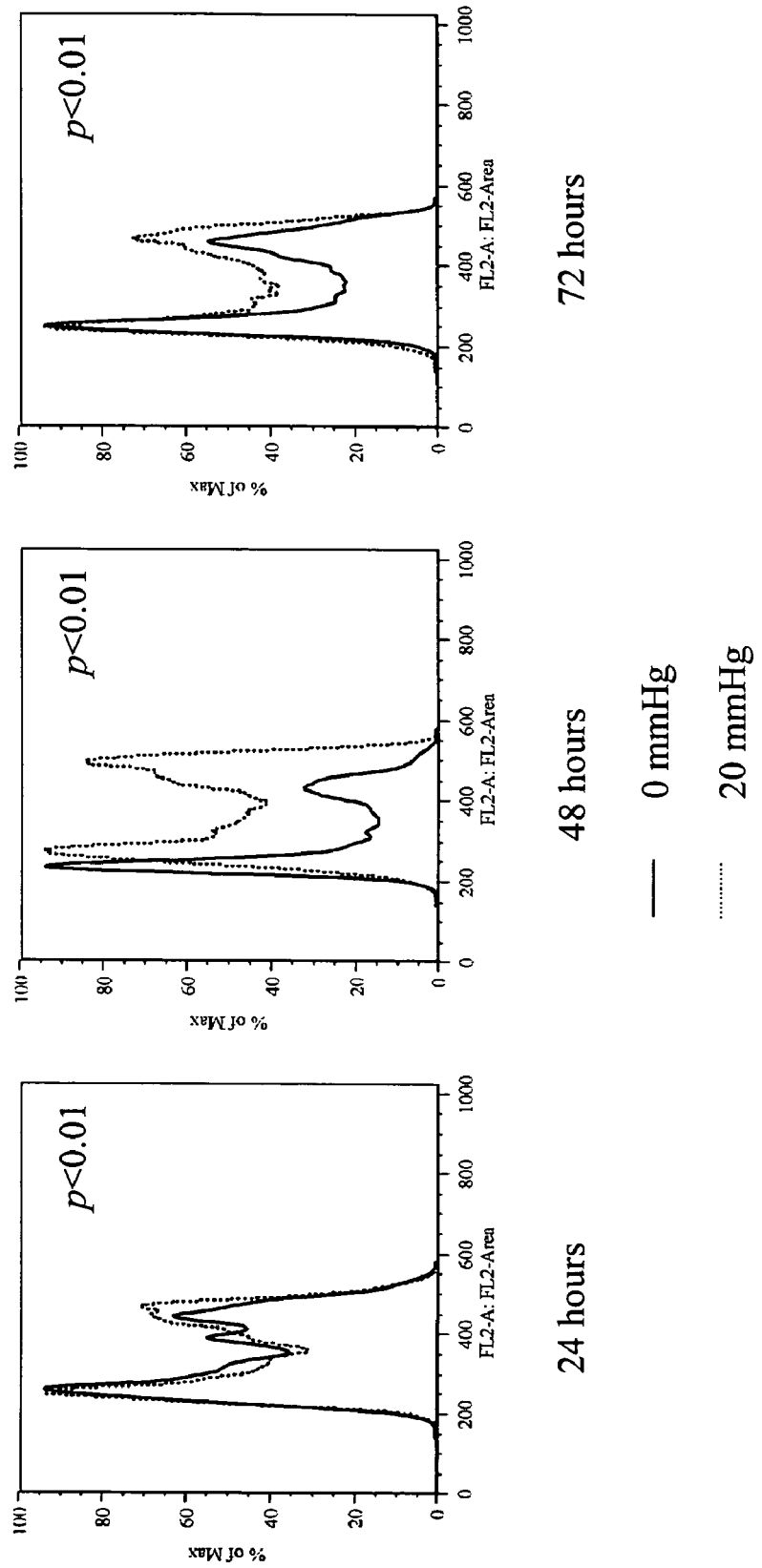

FIGS. 7a. and 7b. Cell cycle analysis of HOS cells grown at two pressures. (a) Each line plot represents the concatenated results of three experiments. (b) Percentage of cells in S phase is derived from the Dean-Jett-Fox cell cycle algorithm. These results show that under pressure the cells become more proliferative as evidenced by an increasing proportion of cells in S phase.

Figure 8A:
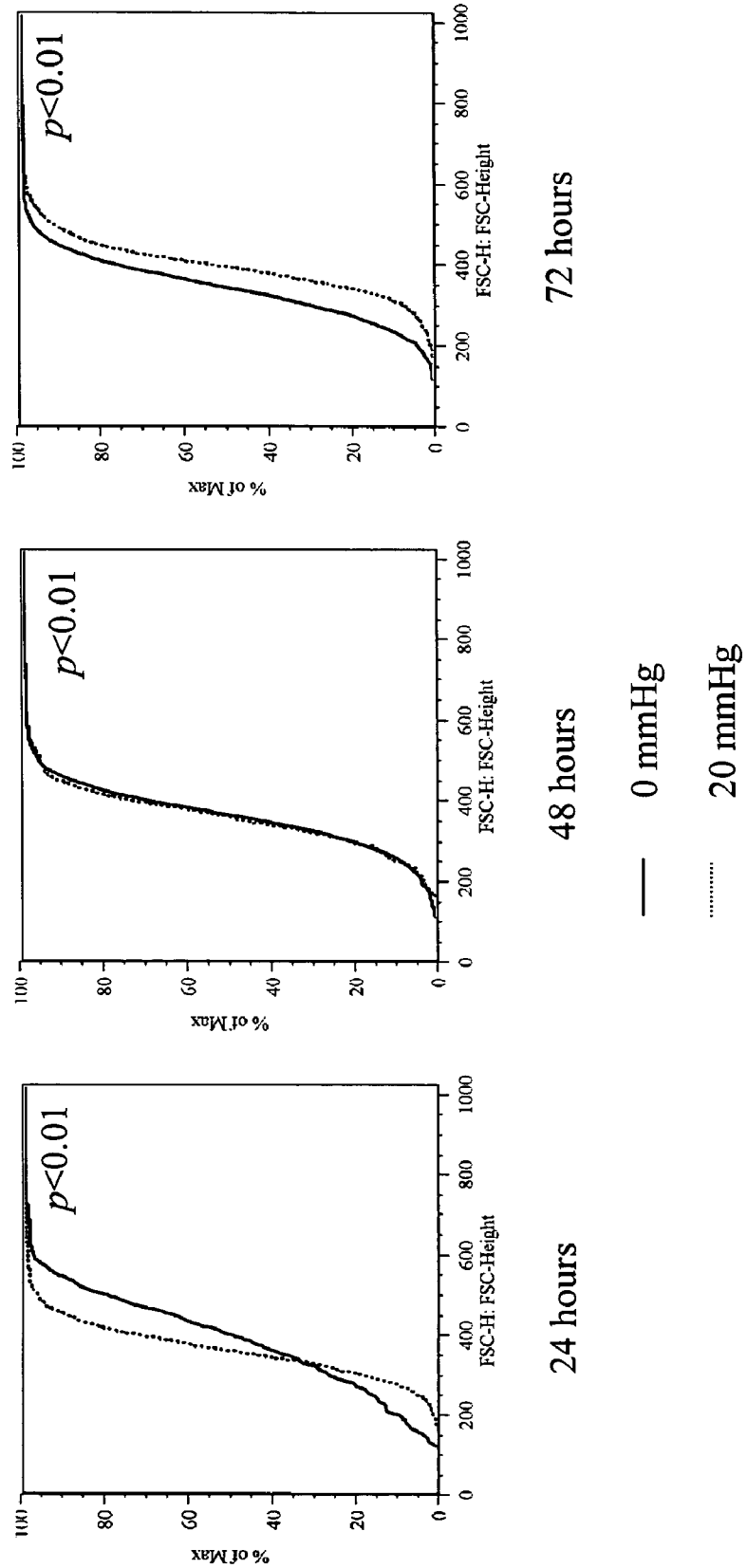

FIG. 8a. With Pressure the cells appear to become larger, 8b. With pressure the cells become more granular as estimated by the side scatter profiles. Forward scatter (FSC) and side scatter (SSC) of HOS cells G1 of the cell cycle grown under pressure 0 and 20 mmHg. The top row (a) shows that with pressure the cells appear to become larger. Similarly with pressure the cells become more granular as estimated by the side scatter profiles as shown in the bottom row (b). One possible interpretation of this is that the cells under pressure are in a more proliferative and dynamic state and hence synthesizing more cellular constituents in preparation for cell division.

FIG. 9. Relationship of cell death under 2 pressures with time. Cell death is reflected by the pre-G1 gated event frequency of cell cycle analysis. This shows that with increased pressure the amount of death generated in the system is increased. Whether this is a function of cell proliferation or the increased pressure per se is uncertain.

Figure 10:
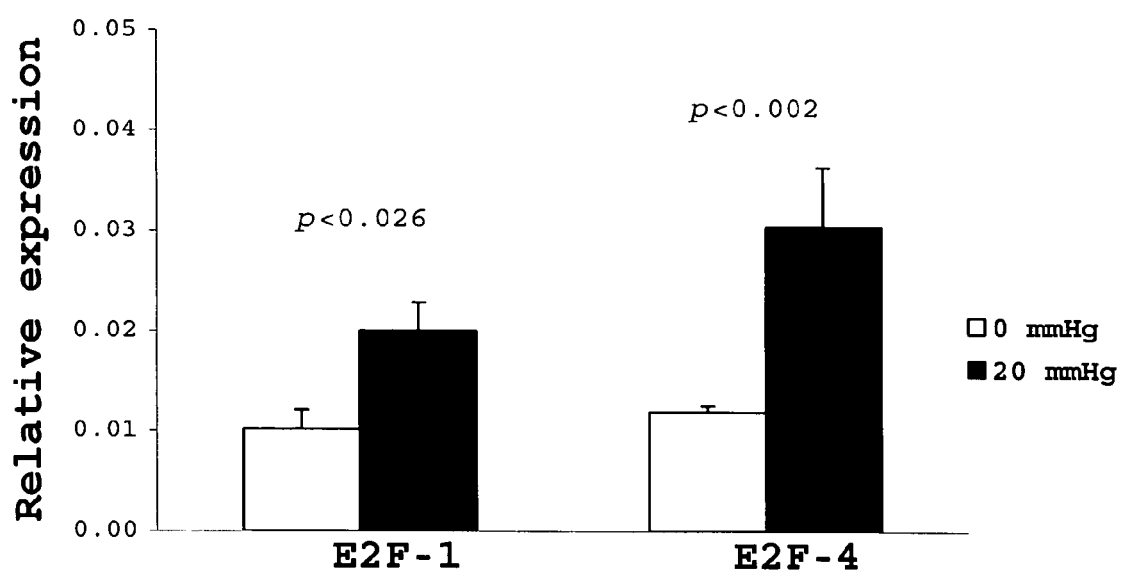

FIG. 10. Relative expression of E2F1 and E2F4 at 0 and 20 mmHg. The significant up-regulation of these cell related transcription factors confirms the finding that pressure induces an increased state of proliferation.

Figure 11:
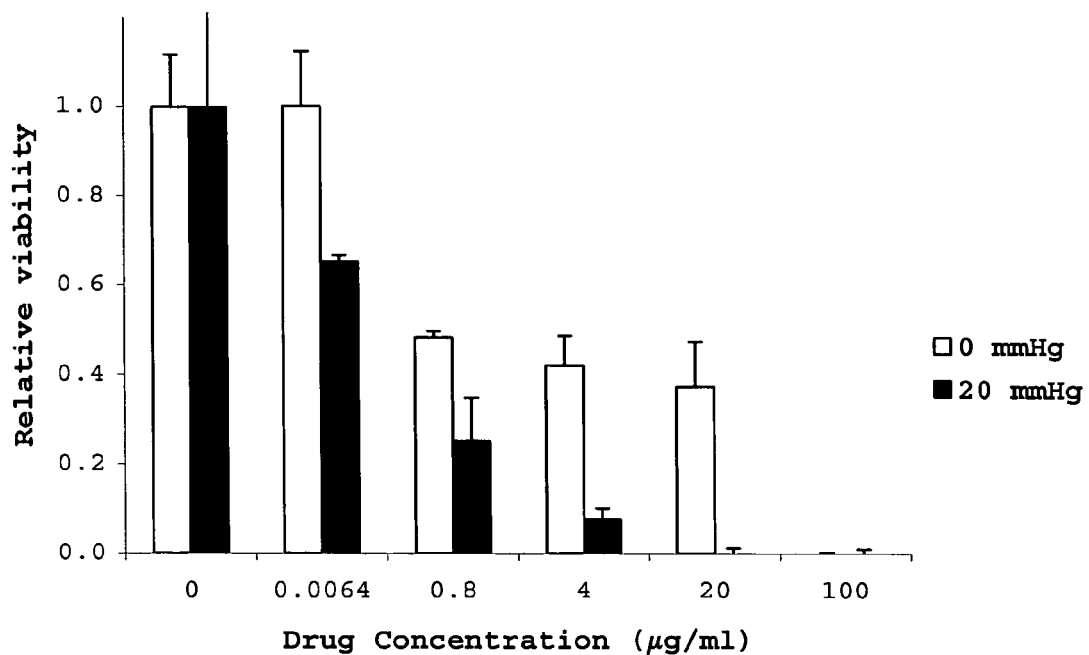

FIG. 11. HOS cells grown under pressure for 72 hours, cut from membranes and exposed to serial dilutions of doxorubicin for 24 hours. Testing was done at atmospheric pressure but the membranes bearing the pressurized cells were immediately exposed to doxorubicin. The differences exhibited in FIG. 13 are now more distinct. The simple omission of a 24 hour period of de-pressurization to allow cell reattachment confers dramatic differences to sensitivity. This suggests that chemosensitivity testing should be performed under pressure.

FIG. 12a. Doxorubicin cytotoxicity with depressurized cells and 12b. Cisplatin cytotoxicity with depressurized cells. Conventional chemosensitivity testing of HOS cells grown under pressure with (a) doxorubicin and (b) cisplatin. Testing was done at atmospheric pressure. There is a statistically significant difference in cytotoxicity ($p<0.05$) in the clinically relevant drug concentration range of 0.04 to 4 µg/ml.

FIG. 13a. HOS cells grown under pressure and exposed to serial dilutions of doxorubicin and 13b. HOS cells grown under pressure and exposed to serial dilutions of cisplatin. Chemosensitivity testing was done under pressure. In this proposed method of assessment cell viability is assessed by cell counts under pressure. The dramatic difference in viability in the clinically relevant range of 0.04 to 4 µ/ml again serves to illustrate the importance of chemosensitivity testing under pressure. This provides some insights into the sensitivity of tumors in the in vivo setting—they may be more sensitive to chemotherapeutic agents under pressure but are subjected to limited delivery of these drugs due to reduced perfusion.

FIGS. 14a., 14b., 14c. and 14d. Apoptosis assay of (a) non-pressurized, (b) pressurized and (c) positive control. (d) Genomic DNA gel electrophoresis. Apoptosis was not demonstrated in cells grown under pressure or those not grown under pressure. Apoptosis (green fluorescence) was reliably demonstrated in the positive control. Cell death within the pressurized systems is therefore believed to be due to necrosis.

Figure 15:
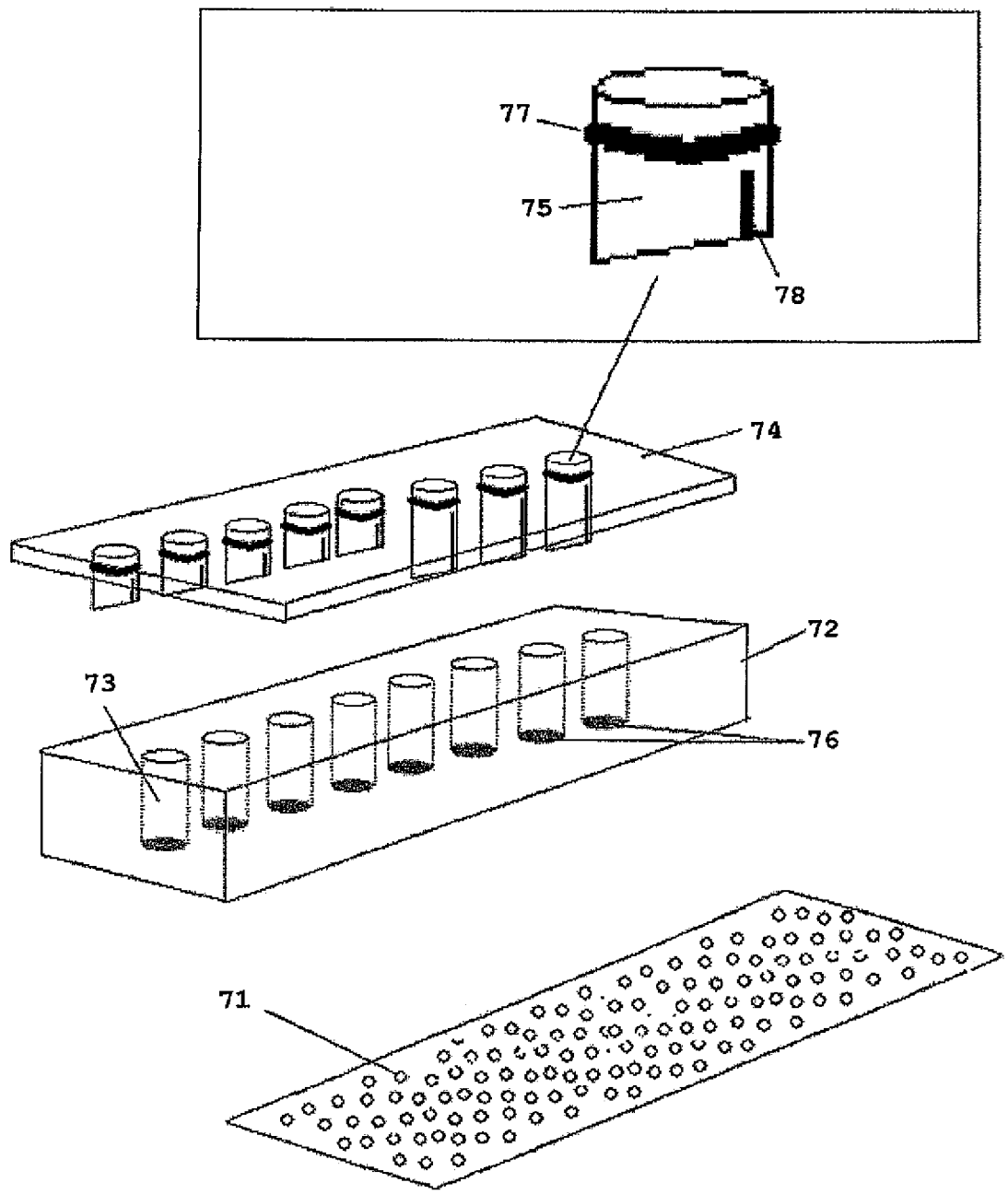

FIG. 15. Pressurized Multi-Well Cell Culture Cluster. This figure shows the prototype for a new device for growing tumor or other cells under hydrostatic pressure which can be useful for screening chemotherapy drugs. The design shown has eight (8) growth cylinders, however, it can be fabricated with as many as needed, for instance, 98, the number of wells in the un-pressurized units.

DETAILED DESCRIPTION OF THE INVENTION

This invention provides an apparatus for growing cells under pressure comprising a cell culture cassette having a matrix for cell growth, two side assemblies which include a frame with a rigid support that fits over the cell culture cassette solid, with said assemblies positioned on either side of the cassette over the solid support sides, and a means to secure the sides of the cassette.

This invention provides an apparatus for growing cells under static or dynamic physiological pressure, comprising:

(a) a cell culture cassette 12 comprising a cassette frame 13; two side walls secured to each side of the cassette frame to form a cell growing chamber; and a means 4, 5, 10 for adjusting fluid pressure or flow, for providing culture media or cell culture, or for sampling cell culture or culture media within the cell growing chamber, wherein at least one side wall comprises a cell growth surface;

(b) an adapter 21, also referred to herein as "High Pressure Adapter", comprising two side assemblies 24 with each side assembly comprising a frame with a rigid support that fits over the cell culture cassette, wherein said side assemblies are pivotably attached at one end and positioned over the two side walls of the cell culture cassette; and (c) a means 43, 52 to secure the two side assemblies over the two side walls of the cell culture cassette.

In an aspect of the present invention, the cell culture cassette of the present invention can be fabricated to assume various shapes, such as a cylinder or 3-D disc, dimensions or sizes based on the intended application(s) of the cell culture cassette and High Pressure Adapter. The design parameters, including the distances between the walls or sides of the cell growing chamber, for constructing an appropriate or suitable cell culture cassette would be apparent to one of ordinary skill in the art. For example, cylindrical-shaped cell culture cassettes will be optimal for flow-through large-scale experiments. In another example, smaller cell culture cassettes will be useful where the cost of performing the studies or where difficulties in obtaining reagents or cell cultures are a factor. In a further example, a flat flow-through cell cassette design may be useful for screening many drugs at once. In a further example, the distances between the walls or sides of the cell culture cassette may be dependent on the metabolic activity of the cell culture, whether media change can be performed, or whether the cells will attach to the cell growing surface, etc. The High Pressure Adapter may be fabricated by one of ordinary skill in the art to accommodate the various possible cell culture cassette designs or can also be incorporated with the cassette concept to create a high-pressure cassette.

In an embodiment, the matrix for cell growth is a membrane. In a further embodiment, the membrane is a fiber-reinforced membrane. In a still further embodiment, the fiber is metal or organic based. The metals can be stainless steel, platinum, gold, titanium or other biocompatible metal.

In a separate embodiment, the matrix is composed of beads. In another embodiment, the matrix is nylon-based. As known in the art, a variety of matrices can be used in this invention.

In an embodiment of the above apparatus, the cassette contains a means to facilitate imposition of fluid pressure. In a further embodiment, the means is a luer valve fitting to apply hydrostatic pressure. In a further embodiment the cassette contains baffles 31 at both short sides of the cassette. The intent of the baffles is to create a laminar flow profile through the cassette thereby reducing shear associated with turbulent flow that may damage cells. Alternatively, if required, this design allows the simultaneous application of shear and hydrostatic pressures to simulate the environment that exists within the lumen of blood vessels. In addition, the uniform profile will ensure that nutrient distribution is homogenous throughout the cassette without dead zones at any corner of the cassette.

In a separate embodiment, the rigid support of the apparatus contains mesh 22 or external, raised lattice. The mesh or lattice may be made of plastic or stainless steel, platinum, gold, titanium or other biocompatible metal.

It is not necessary that the rigid support contains mesh but more importantly it is the coverage of the matrix on which the cells are growing. In an embodiment, the percentage of coverage of the matrix may be up to 20%. In another embodiment, the coverage is up to 50%. In a separate embodiment, the coverage is up to 70%.

In an embodiment connecting to each side frame is a valve support which mates with an infusion part.

The above-described apparatus may be made of plastic or stainless steel or other materials which can stand high or negative pressure.

In an embodiment, the apparatus is depicted in FIG. 2.

This invention also provides a method of growing cells Under static or variable pressure comprising steps of:

(a) seeding said cells in the fluid growth media within cassette;

(b) placing the cassette of step (b) into the above-described apparatus; and (c) applying static or dynamic hydrodynamic pressure via the side port on the cassette or through the rubber stop on top of the cassette.

The cells include but are not limited to normal cells such as cartilage, endothelial, or muscle cells, bacteria, yeast or various tumor cells. In an embodiment of the tumor cells, the tumor is an osteogenic sarcoma.

The static pressure ranges from negative to 150 mmHg and could be higher with appropriate rigid materials. Appropriate pressures may be selected based on the physiologic cardiovascular pressure changes in arteries or veins.

This invention provides a composition comprising cells grown by the above method. This invention also provides a composition comprising the extract of cells grown by the above method(s).

When desirable, i.e. culture of electrically sensitive cells, an electric field can be applied across the membranes via the metal screens that supply structural support for elevated pressure. The electrical potential is applied via electrical connections attached to the screens. The field strength selected depends upon the cell type. Alternative metal screen designs are possible to a user skilled in the art such that two or more electrodes can be placed on a single side of the adapter, e.g. the metal screen is divided into two or more sections. The individual sections can be fixed to the high pressure adapter frame by additional fasteners or by the use of non-conductive joints holding the metal sections together into one section. Such arrangements will enable the creation of fields affecting cells attached to different locations upon a single membrane side of the cassette.

The invention disclosed herein refers to an adapter that is positioned over any cell cassette with gas permeable membrane sides to facilitate cell culture at elevated media pressures. The adapter is comprised of three components and is shown in FIG. 2. The components include two side assemblies that are positioned on either side of the cassette over the membrane sides, and a holding assembly, i.e. multi-cassette holder, slide closure or spring clip to secure the sides to the cassette. The side components include a frame with a rigid stainless steel mesh that fits above the cell culture cassette membrane and a valve support on the top of each side frame that mate with the infusion port. The mesh can be selected from a variety of openings. The adapter allows for movement of gas to the membrane and the application of pressure to the internal media without creating a bulge in the membrane ensuring a constant media volume. Further, the valve supports permit the secure location of two 3-way valves for communication with the media and application of pressure. The adapter can be made from rigid plastic, i.e. delrin, or metal, i.e. stainless steel.

Also disclosed herein is a new cassette design that includes a screen support over two membrane side windows to buttress the membrane for high pressure application. The screen can be made from the same material as the cassette frame or with stainless steel. The cassette design will also include two fluid entry luer valve fittings to facilitate flow through capability at elevated hydrostatic pressures without leakage. Within the cassette are baffles to direct flow and avoid dead zones. The intent is to duplicate the functionality of the adapter described above for low pressure cell culture with a new cassette expressly designed for high pressure cell culture. This high-pressure cassette integrates the essential features of the low pressure cassette adapter used to enable a low pressure cassette to function under high pressure conditions (FIG. 3).

Also disclosed herein is an alternative method of varying pressure within the cassette with High Pressure Adapter. FIG. 6 shows an alternative approach to apply constant or variable pressure to the fluids within the cassette placed in the high pressure adapter. The approach takes advantage of the metal screen in contact with the membrane film of the cassette. Pushing on one screen with an external device causes fluid within the cassette to compress and subsequently pressure to increase. The types of external devices that could be used to push against the screen include fluid filled piston, electronically controlled solenoid, balloon, or any other linear motion device. The temporal characteristics of the pressure waveform imposed on the fluid are dependent upon the linear motion of the external device. This approach uses two fluid filled pistons applying pressure to the steel sides of the high pressure adapter of four cassettes. The fluid used is gas, i.e. air. A computer controls the valves and timing.

Pressure is provided to the cell culture cassette via a passive water reservoir or a computer controlled pressure regulator attached to the reservoir to create a static or variable pressure head, respectively to the growth media. In addition to simulating the in vivo elevated pressure conditions of growing tumors, pressure regulation also ensures that the media fluid volume within the cassette is constant as water evaporates across the membrane. FIG. 5 is a schematic drawing that shows the cell culture cassette and pressure regulation assembly. This approach is suggested because the outlet from one reservoir can be connected to a multi-port manifold and connected to several cell culture cassettes simultaneously. If a time-varying pressure waveform is desired, the computerized pressure controller can add a time-varying component to the static pressure head and simulate an in vivo pressure waveform. The regulator shown in the FIG. 5 utilizes an oscillating piston that adds or removes fluid from the reservoir to increase or decrease the static pressure head. This approach is one of many approaches that can be used to vary reservoir pressure. The "Connection Valve" permits connection of a cell culture cassette to the reservoir manifold and pressurization of the cassette when it is turned on. The "Sampling Valve", when opened, can be used to obtain media samples for analysis or cell harvest. Gas and temperature regulation within the cell culture cassette is accomplished by placing the cassette and tubing within a temperature-controlled incubator with provision to accommodate pump tubing.

Intended Use/Applications

The cell culture cassette high-pressure adapter is designed to enable the culture cassette to grow cells in a pressure-controlled environment; The high pressure cassette design can be used directly. High-pressure capability is especially important for solid tumor cells that grow under conditions of elevated interstitial fluid pressure. Applications for this invention include the determination of tumor cells' gene expression as a function of growth pressure, to assess an individual patient's tumor chemo-sensitivity, observe changes in cell morphology, and changes in cell proliferation rates. Three dimensional clusters of cells, i.e. spheroids, can be grown within the cassette by pre-coating the inner surface of the membranes with a thin film of gel, e.g. agarose. Spheroids more closely simulate the cell-cell interaction within tumors than planar sheets of tumor cells. The cassette-HPA approach allows the growth of spheroids under elevated pressure.

Interstitial Fluid Pressure

The relevant magnitude and range of interstitial fluid pressure (IFP) in cancers was established from direct tumor measurements of IFP in osteosarcoma patients. The hydrostatic pressure effect on cancer cell population dynamics was defined using a newly designed cassette-HPA cell culture system to simulate interstitial conditions.

The clinically relevant range of pressure was recreated in vitro (0, 20, 50, 100 mm Hg) within the cassette-HPA system to characterize population dynamics of three human osteosarcoma lines (HOS, U2OS, and SaOS2), a breast adenocarcinoma cell line [MCF7], and a non-small cell lung cancer cell line [H1299]. The latter two cell lines were selected because these tumor types frequently metastasize to bone. It was determined that the influence of hydrostatic pressure was cell type specific and a function of pressure magnitude. Proliferation rates for MCF7 and H1299 were faster at 20 mmHg than a 0 mmHg; HOS and U2OS' rates were faster at 50 mmHg than at 0 mmHg; SaOS2's proliferation was most robust at 0 mmHg. A logistic equation was used to estimate proliferation rates. Cell death was not associated with apoptosis.

Elevated interstitial fluid pressure (IFP) observed in solid tumors (5) is most likely the consequence of the abnormal development of the tumors' vasculature and the absence of a functioning lymphatic system. The values that have been observed typically reflect the arteriolar pressure component of the tumor's vascular network (4) and the tissue's elasticity (3).

Elevated IFP is a generalized phenomenon, confirmed in most solid tumors. Nevertheless, tumor cell biology and therapeutics are routinely studied in non-physiologic conditions using in vitro cell culture systems at atmospheric pressure. It is unclear how these artificial conditions contort the results of cancer cell studies. Recent investigations report findings using the first mechanical system to evaluate the influence of physiologic pressures on cultured cancer cells.

The effect of elevated fluid pressure has been investigated in various non-neoplastic systems (12, 13, 14). Those investigators who have attempted pressurized cell cultures for non-neoplastic cells have elevated the growth media's fluid pressure by increasing the incubator's gas mixture pressures. While this approach elevates the media's fluid pressures it also elevates the gas concentrations within the media in accordance with Henry's Law. The resulting media gas concentrations are not physiologic and influence important parameters such as pH. This effect requires adjustments to the media buffer mixture composition that complicate the generation of compatible controls.

Cell proliferation studies were performed using human OS cell lines grown within cassettes modified to accept a hydrostatic pressure source and a high-pressure adapter [HPA] to determine the influence of the HPA on gas exchange within the cassette.

Operative Conditions

The operating parameters that are adjusted to properly grow cells within the cell culture cassette with the HPA installed include: 1) Fluid pressure applied to the cell culture media. This pressure is selected by the investigator based upon the experimental conditions desired and can range from 0 to 150 mmHg (gauge). Pressure is adjusted using the height of the passive water head. The computerized pressure regulator can create a time varying pressure with a frequency of range of 0 to 2 Hz. 2) Gas mixture and temperature applied to the incubator: Both of these parameters depend upon conditions selected by the investigator and must be consistent with viability of cells and experimental design.

The invention will be better understood by reference to the Experimental Study Details which follow, but those skilled in the art will readily appreciate that the specific experiments detailed are only illustrative, and are not meant to limit the invention as described herein, which is defined by the claims which follow thereafter.

EXPERIMENTAL STUDY DETAILS

Five studies are presented to facilitate the description and understanding of the invention. They are: 1. Human Osteosarcoma IFP Measurements to identify the pressure range for the subsequent in vitro cell culture studies; 2. Cassette-HPA Characterization Studies to investigate the performance of and identify operational parameters for the cassette-HPA assembly; 3. Cell Proliferation Study to investigate the influence of hydrostatic pressure on tumor cell line growth; 4. Cell Cycle Analysis Study to investigate the biological basis for the proliferation study finding; and 5. Influence of Hydrostatic Pressure on Tumor Cell Response to Chemotherapy to illustrate the clinical importance of including hydrostatic pressure as a cell culture condition when studying drug-tumor cell interaction.

Materials & Methods

Experiment 1

Human Osteosarcoma IFP Measurements

The human osteosarcoma study data presented herein were collected by retrospective review of patient records approved by the Memorial Sloan Kettering Cancer Center Institutional Review Board.

a. Wick-In-Needle Probe:

The Wick-In-Needle probe (WIN) (6) was used to measure IFP within normal tissues and tumors. The device is robust, inexpensive, and capable of accurate, continuous measurement of a tumor's center IFP. Its spatial resolution is dependent upon the length of its side hole, i.e. it will average the pressure over the length of the side hole and reduce the true pressure gradient. Its temporal resolution is primarily dependent upon the density of its packing material. The probes used in this study were fabricated from 22 gauge, 8.9 cm long spinal needles. A 0.4 mm wide slit was machined across the needle shaft, 3 mm from its insertion tip. The wick material used within the needle lumen was 3.0 multi-braid surgical silk. After insertion of the wick material, the insertion bevel was sealed with waterproof epoxy. The typical response time of the WIN probes was under 2 seconds. The WIN probe was connected to a standard Camino 420 pressure sensor (Camino Laboratories Inc., CA) modified to accommodate the luer end of the needle.

b. IFP Measurement Procedure:

IFP was measured in patients at the time of their open biopsy procedures (9). Patients were anesthetized and prepared for their surgical biopsy. Routine incisions were used that would be encompassed by subsequent incisions for limb preserving surgery. Prior to exposing or entering the tumor, measurements of IFP were made first in exposed normal muscle adjacent to the tumor and when possible in normal bone that would be resected along with the tumor. Normal bone was not sampled to avoid the potential spread of cancer cells to uninvolved areas. The WIN probe was introduced into the muscle tissue and the pressure reading was allowed to stabilize, usually within 10 seconds. Normal bone IFP measurements were made next. IFP measurements were then performed in a central tumor region adjacent to the normal tissue site. For normal bone and tumor measurements, a small pilot hole was made into the matrix using a 20 gauge spinal needle or 3/64" drill. This hole was necessary to protect the probe from damage or breakage during insertion through the bony matrix. In these measurements, bone wax was used to seal the gap around probe. Tumor measurements were obtained from a depth of 1 cm into the tumor. The pressure was followed continuously until a stable reading was observed, usually within 2-5 minutes. The total measurement procedure typically required a total of 10-15 minutes to perform.

Procedures Common to Cell Culture Experiments a. Cell Lines and Loading:

The cell lines investigated in this study were a) the HOS, U2OS and SaOS2 osteosarcoma (OS); the MCF7 breast adenocarcinoma; and H1299, a non-small cell lung cancer line (ATCC, Inc.). These were all derived from human tumors and have been cultured at 0 mmHg for many generations.

The cell culture cassette was filled with 10 mL MEM-alpha growth media that included 20% fetal calf serum with penicillin/streptomycin antibiotics. Each cassette was inoculated with 150,000 OS cells; or 500,000 MCF7 cells or 100,000 H1299 cells and placed in a horizontal position within the hotel as shown in FIG. 4A. They were not flipped to ensure cellular attachment onto only one surface. The populated hotel was then placed into a Sanyo Model MCO-20AIC incubator adjusted to 37° C., 100% relative humidity with a 5% CO2, 21% O2, balance N2 gas mixture at 0 mmHg pressure for 24 hours to allow cell attachment to cassette membrane.

b. Cassette Pressurization Levels:

Static pressures, normal to the growth membrane and without a shear component, were transmitted to the cells growing on the cassette membrane. This pressure is similar to the static fluid pressure component experienced by a differential shell of cells within a solid tumor. As a first approximation, the equilibrium pressure gradient within a solid tumor can be modeled using a spherical tumor with concentric tissue shells at different static pressures, with the highest pressure in the core and decreasing pressures within outer shells until the normal adjacent tissue boundary is reached. This concept was introduced by Baxter and Jain (2). However, the steepness of this pressure gradient is a function of tumor type (6). The apparatus was set up to deliver hydrostatic pressure at 3 levels. These were 0 mmHg (comparable to conventional culture systems), and 20 and 50 mmHg. These values were selected because they bracket the IFP range measured in the human OS tumors. The U2OS, SaOS2 and HOS cell lines were studied under these conditions. HOS cell line was further exposed to 100 mmHg, to identify the level of pressure that would reduce its population counts over the study period. The MCF7 and H1299 were subsequently studied using 0, 20 and 100 mmHg hydrostatic pressure.

c. Counting Procedures:

Cell population was estimated using high power field cell counts [100×] obtained from 5 locations on the cassette membrane in a cruciform pattern, i.e. 1 cm from the center of each side and from the center of the growth membrane. This field corresponded to a membrane area of 2.6 mm$^2$. Measurements were made with the high pressure adapter removed from the cassette. Counts were made at 24, 48 and 72 hours after pressurization. At each time point, one cassette from each pressure group was depressurized by disconnecting its manifold line and removing the high pressure adapter. This cassette was sacrificed to determine a retrieval viable cell count. Only one membrane was used in our study to facilitate photographing the cells present on the growth surface and high power field counting.

Measurement of retrieval viable cell count required harvesting the cells attached to the cassette membrane. Cells within the cassettes were first rinsed with phosphate buffered saline (PBS), then 3 mls of 0.25% Trypsin-EDTA was injected and the chamber incubated for 5 minutes. The chambers were next injected with 7 mls PBS and the mixture eluted from the cassette. The suspension was removed from the chamber, placed into 15 ml Falcon tubes and centrifuged at 1,500 RPM for 5 minutes. The supernatant was discarded and the pellet re-suspended in 1 ml PBS. The viable cells were counted using a hemocytometer (Bright-Line®) with Trypan Blue; viable cells do not take up the stain. The experimental procedure was repeated 3 times for each cell line.

d. Mathematical Analysis of Cell Proliferation:

The estimation of doubling time, one index of cell proliferation, was performed with the cell count data using a form of the Logistic equation appropriate to this study. It is shown below as Equation 1:

$$C(t) = C_{max} * C_0 / (C_0 + (C_{max} - C_0) * \exp^{(-0.693 * t / T_d)}) \quad \text{(Equation 1)}$$

where $C_0$ is the initial cell population; $C_{max}$ is the viable cell population equilibrium between the birth and death processes; and $T_d$ is the doubling time. Non-linear parameter estimation was performed to fit the cell count data to Equation 1.

Experiment 2

Cassette-HPA Characterization

The HPA design reduces the exposed membrane surface area of the cassette and may reduce the trans-membrane gas exchange of the cells with the incubator atmosphere. The influence of the HPA on cell population was studied using three experiments. The population change of the U2OS and SaOS2 cell lines grown at 0 mmHg within T75 flasks, cassettes alone, and cassettes with the HPA were first compared to confirm that Osteosarcoma cells would, in fact, grow within the cassette assembly and to determine the study duration time for future studies. The U2OS and SaOS2 cells were allowed to incubate for 168 and 144 hours after pressurization, respectively without media change. Retrieval viable cell counts for the U2OS were obtained at 48, 96 and 168 hours and at 24, 72 and 144 hours for the SaOS2. The criterion for selecting the duration was that time when the cell count approached a plateau, i.e. before confluence. Continuing a study beyond this point would result in cell death due to inadequate nutrient supply.

A second experiment, performed using SaOS2 cells grown at 0, 20 and 50 mmHg, measured the media pH at the start of the study and again at the conclusion of the 72 hour time point.

A third characterization experiment was performed to measure the influence of HPA on the rate of oxygen movement into the fluid media through the cassette membrane. This experiment was performed using saline at 21.6° C. deoxygenated by continuously bubbling 100% $N_2$ for 30 minutes. Media was not used because significant foaming would-have resulted from the bubbling $N_2$. A cassette was modified to accept a calibrated FOXY® fiber optic oxygen optode (Ocean Optics, Inc.; Dunedin, Fla.) positioned in the center of the cassette. This optode measures $O_2$ continuously without consuming it and has a response time of several seconds. The cassette was filled with deoxygenated saline and the optode measured levels of dissolved $O_2$ within the saline as $O_2$ from the surrounding air diffused across the membrane and through the fluid to the optode. The experiment was terminated when the optode signal stabilized at 21%, the atmospheric concentration of oxygen. The experiment was repeated using the same cassette with fresh deoxygenated saline and an HPA in place. The recorded data was analyzed using Equation 2

$$P = P_0 + P_{max} * (1 - \exp^{(-T * \ln(2)/t_{1/2})}) \quad \text{(Equation 2)}$$

to compute the time constant, $t_{1/2}$, of oxygen movement into the saline within the cassette. In this equation, $P_0$ and $P_{max}$ are the dissolved $O_2$ (units=%) within the saline at t=0 and at t=∞, respectively.

Experiment 3

Cell Proliferation Study

Cell proliferation is the sum of birth and death processes occurring within the cassette-HPA chamber by a population of cells in various stages of the cell cycle. Using the experimental conditions determined from the characterization studies, proliferation studies were performed to compare the influence of hydrostatic pressure on the 5 human tumor cell lines, HOS, U2OS, SaOS2, MCF7, and H1299.

Influence of Hydrostatic Pressure on Cell Cycle Analysis (Experiment 4.) and Tumor Cell Chemosensitivity (Experiment 5.):

The data presented in Experiments 2. and 3. suggest that the gene expression of these cells may be influenced by elevated interstitial pressure and this expression alters the cells' response to chemotherapy. Two experiments were designed to investigate these possibilities, i.e. Experiment 4. Cell Cycle analysis and Experiment 5. Influence of Hydrostatic Pressure on Tumor Cell Chemosensitivity. Experiment 4. includes experiments to determine if cell death occurred through the apoptosis pathway.

Experiment 4

Cell Cycle and Apoptosis Analysis

The HOS cell line was used. It was pressurized at 0, 20, and 50 mmHg for 24, 48 and 72 hours. These cells were then harvested and prepared for cell cycle analysis. Cells were fixed in 66% methanol and 33% PBS, then treated with 100 U/ml ribonuclease and DNA florescent labeled with 0.05 mg/ml propidium iodide. Morphological cell cycle parameters were measured by flow cytometry using the FACS Calibur System (BD Biosciences, Franklin Lakes, N.J.). Data was analyzed using FlowJo 4.3.1 (Tree Star, Ashland, Oreg.). Forward and side scatter profiles delineated cell morphology. Cell cycle analysis was performed by analyzing the FL2-A profile of the cells identified to be in cycle. Gating for cells in G1 provided a subpopulation of cells which were relatively more stable in terms of cell division. This subpopulation was assessed for forward scatter and side scatter characteristics.

Quantitative Real Time Polymerase Chain Reaction:

HOS cells were pressurized for 72 hours, released from culture and immediately treated with RNA lysis buffer. RNA was extracted with the Stratagene RNA Isolation Kit® (La Jolla, Calif.). The Promega Reverse Transcription System® (Madison, Wis.) was used to synthesize cDNA. Standardization and validation of the assays have been previously described[1]. Briefly, 5 μl of cDNA were added to 20 μl of separate aliquots of master mix containing primer and probe sequences for E2F-1 and E2F-4 and the reference housekeeping gene β-actin. Realtime PCR with the iCycler® (Bio-Rad, Hercules, Calif.) was performed. Cycling parameters were as follows: one 10 minute hot start at 94° C.; 45 cycles of 30 second denaturation at 94° C.; 1 minute of annealing at 55° C.; 30 second extension at 72° C. and a final 5 minute extension at 72° C. Each sample was run in triplicate for both the target gene and the housekeeping gene. This data was normalized to the gene expression of a control known to express E2F-1 and E2F-4. The control used was a laboratory grown osteogenic sarcoma cell line designated M187 which was treated in the same way and in the same PCR reaction in a 96-well plate. The method for analyzing real-time PCR data has been described previously[1]. Significance testing was performed with the Wilcoxon two sample test.

Apoptosis Assay:

The Oncogene FragEL® (San Diego, Calif.) kit was used to assess for apoptosis. This is an assay which uses terminal deoxynucleotidyl transferase similar to the TUNEL assay. HOS cells were grown under 0 and 20 mmHg pressure for 24 hours. In addition an apoptosis control consisted of HL60 cells incubated with 0.5 μg/ml actinomycin D for 19 hours to induce apoptosis and untreated HL60 cells. All cells were fixed in 4% formaldehyde in 1×PBS and rinsed with 1×TBS. The cells were permeabilized with proteinase K, incubated at room temperature for ten minutes and rinsed with 1×TBS. Each sample was then treated with a TdT equilibration buffer and incubated at room temperature for 30 minutes. The sample was incubated with a TdT substrate labeling reaction mixture for 1 hour at 37° C. Cells were triple rinsed with 1×TBS, counterstained with DAPI and stored at 4° C. in the dark. Slides were read with a standard fluorescence microscope with a DAPI filter for nuclear localization and a fluorescein filter for green fluorescence.

The results of the apoptosis assay were corroborated using DNA gel electrophoresis of genomic DNA. DNA was extracted using the DNeasy tissue kit® from Qiagen (Valencia, Calif.). HOS cells were pressurized at 0 and 20 mmHg as above and released from culture. They were centrifuged at 300×g and the pellet re-suspended in 200 μl PBS. 20 μl proteinase K and 200 μl buffer was added and the mixture incubated at 70° C. for 10 min. The mixture was centrifuged through a spin column after adding 200 μl 100% ethanol. Final elution into a microcentrifuge tube was done at 6000×g for 1 minute. DNA gel electrophoresis was performed with ethidium bromide fluorescence using a 100 kbp comparison standard.

Experiment 5

Influence of Hydrostatic Pressure on Tumor Cell Chemosensitivity a. Chemosensitivity Testing Using a Conventional 96-well Plate:

HOS cells were pressurized at 0 and 20 mmHg for 72 hours. At the end of this time point the growth membrane was removed and discs were created with a sterile punch. These discs bearing 2000 cells/disc were placed within each of the wells in a Costar 96-well plate (Bio-Rad, Hercules, Calif.). Serial dilutions of doxorubicin were immediately applied to the wells at a dose of 100 μg/ml to 0.00128 μg/ml. These were allowed an exposure time of 24 hours and then washed with PBS and 200 μl growth media replaced for a further 24 hours 25 μl of Alamar blue dye® (BioSource International, Camarillo, Calif.) was added for a further 8 hours and metabolic activity read with a Cytofluor® plate reader (Applied Biosystems, Foster City, Calif.). Metabolic activity was expressed as per manufacturer recommendations (BioSource International, Camarillo, Calif.).

The experiment was repeated using cells grown at 72 hours under pressure, de-pressurized to atmospheric pressure and then trypsinized and seeded at 2000 cells per well and allowed 24 hours to gain attachment. They were then treated with doxorubicin. Assessment was completed as above. A similar set of experiments was performed to assess for cisplatin sensitivity under pressure. Student's t-test was used to assess for significance between the results of chemosensitivity at 0 and 20 mmHg. This data is represented in FIG. 12. Each data point represents the mean of six readings with error bars representing the standard deviation.

b. Chemosensitivity Testing in a Pressurized Cassette-HPA System:

To investigate chemosensitivity in a pressurized system, $1.5 \times 10^4$ HOS cells were seeded in 16 cassettes. These were incubated for 24 hours and baseline counts were made at the end of 24 hours. Serial dilutions of doxorubicin were added at a dose of 0 μg/ml, 0.16 μg/ml, 1 μg/ml and 8 μg/ml. Similarly serial dilutions of cisplatin were added at doses of 0 μg/ml, 0.16 μg/ml, 1 μg/ml and 2 μg/ml. Two sets were provided for each drug at 0 and 20 mmHg. Pressurization proceeded for 72 hours as described above. At the end of this time point, in situ cell growth over the identical 5 high power fields recorded after the first 24 hours were made. The observer was blinded to the identity of the sample being read. Cell growth was expressed as a ratio between the 72 hour and baseline 24 hour counts. This was then normalized to the readings for cells that were not exposed to chemotherapy (i.e. 0 μg/ml). This was done to account for cell growth changes that could result from the pressure effect itself. Student's T-test was used to assess for significance between the results of chemosensitivity at 0 and 20 mmHg. This data is represented in FIG. 13. Each data point represents the mean of five readings with error bars representing the standard error of the mean.

Results

Experiment 1

Human Osteosarcoma IFP Measurements

IFP measured in the central region of 15 histologically confirmed, high-grade osteosarcoma tumors was 35.9±16.2 mmHg (mean±std. dev.). IFP in normal muscle adjacent to the OS tumors, measured in 15 patients, was 5.3±4.4 mmHg (mean±std. dev.). IFP in normal bone, obtained from 6 patients, was 11.8±10.4 mmHg. Tumor IFP was higher than IFP measured in normal bone (p<0.003) and adjacent muscle (p<0.001), respectively. The mean arterial pressure in the patient group was 74.6±10.5 mmHg.

The patient population included 7 males and 6 females whose average age was 20.5±14 years old. Tumor locations were 2 humeri, 4 tibias, 5 femurs, 1 sacrum, and 1 pubis; all were extra-compartmental.

Representative pressures of 0, 20, and 50 mmHg were selected to bracket the spectrum of mean pressures seen clinically; or within the central region and gradient pressure region of OS tumors. These were applied to the pressurized cell culture system.

Experiment 2

Cassette-HPA Characterization Studies

From the first characterization experiment, the 72 hour time point was determined to be a suitable study duration for the HPA experimental design. All subsequent studies were terminated at 72 hours after application of pressure (96 hours after seeding) to avoid the ceiling affect that could occur as cells achieve confluence and because there was no media change. Cells within the 0 and 20 mmHg cassettes approached but did not achieve confluence. In traditional cell culture, media change is possible because the cells are grown un-pressurized in an open system that can proceed for longer periods of time. In pressurized cell culture using the cassette-HPA under "no flow" conditions, a media change would require a period of depressurization. This would introduce a confounding variable to the study The pH of the growth media within the SaOS2 cassettes at the start of the study was 7.71. At the end of the 72 hour growth period, pH dropped to 7.59±0.05, 7.66±0.02 and 7.62±0.03 for the 0, 20 and 50 mmHg cohorts, respectively. The values shown are mean±standard deviation; no statistically significant difference was observed between the pH values of any cohort.

The Equation 2 time constant for oxygen movement into the deoxygenated saline filled cassette was 24 minutes. When the HPA was used the time constant increased to 64.6 minutes. The correlation coefficient ($R^2$) associated with the parameter estimation to compute the time constant were 0.999 and 0.987, respectively.

Experiment 3

Cell Proliferation Study

The Equation 1 population doubling time ($T_d$), and equilibrium cell population ($C_{max}$) parameters along with the correlation coefficient ($R^2$) computed for each cell type's composite data set is presented in the table shown below.

| Cell Line | 0 mmHg $T_d$ (hrs)/ $C_{max}$ $R^2$ | 20 mmHg $T_d$ (hrs)/ $C_{max}$ $R^2$ | 50 mmHg $T_d$ (hrs)/ $C_{max}$ $R^2$ | 100 mmHg $T_d$ (hrs)/ $C_{max}$ $R^2$ |
|---|---|---|---|---|
| HOS | 21.5/ 1.6E+4 0.99 | 24.9/ 3.3E+3 .99 | 20.6/3.E+6 0.99 | 49.0/ 165. 0.99 |
| U2OS | 28.2/ 3E+6 0.99 | 24.5/3E+6 0.99 | 21.5/3E+6 0.99 | |
| SaOS2 | 40.8/ 3E+6 0.99 | 14.3/1.74 0.99 | 10.5/1.44 0.98 | |
| MCF7 | 39.1/ 3E+6 0.98 | 34.7/3E+6 0.98 | | 60.9/ 3E+6 0.98 |
| H1299 | 24./3E+6 0.96 | 23.0/3E+6 0.96 | | 40.8/ 3E+6 .96 |

Regression analysis of data to Equation 1 produced fits with $R^2 \geq 0.96$ for all 16 studies. Applicants observe that the 5 cell lines' proliferation rates behave differently from each other and as a function of pressure. However, the doubling times reported for the cell lines grown under 0 mmHg pressure are equivalent to the doubling time estimates obtained from ATCC Technical Services (Personal Communications), i.e. 24-48 hours for HOS and U2OS; and 48-72 hours for SaOS2, 40 hrs for MCF7 and 20-40 hours for H1299. Of the three osteosarcoma cell lines, the HOS and U2OS cell lines were less sensitive to hydrostatic pressures than the SaOS2. The proliferation rate for HOS was fastest at 50 mmHg but slowest at 100 mmHg. At 20 mmHg, its proliferation rate was slower than at 0 mmHg. For the U2OS, the proliferation rate increased as pressure increased. While the parameter estimation for $T_d$ suggests that the SaOS2 had the fastest proliferation rate, $C_{max}$ was also the lowest, suggesting that birth and death processes rapidly came into equilibrium. Both the MCF7 and H1299 proliferation rates were faster at 20 mmHg pressure than at 0 or 100 mmHg.

$C_{max}$ is 3E+6, the maximum cell count constraint, for the MCF7, H1299 and U2OS cell lines at all pressures; HOS at 50 mmHg, and SaOS2 at 0 mmHg. The value results when the parameter estimation algorithm is unable to estimate a biologically realistic maximum cell count from the data set it is analyzing. This inability suggests that the cell lines exhibited an exponential growth pattern over the duration of the experiment and that growth was the predominate process.

Experiment 4

Cell Cycle and Death Analysis

The cells grown under 20 mmHg pressure were found to be phenotypically distinct from cells grown at atmospheric pressure (0 mmHg). Forward scatter and side scatter profiles of cells in all time points showed that cells in cycle became bigger with pressurization at the 48 and 72 hour time points (p<0.01). FIGS. 8a,b show the forward scatter and side scatter profile of HOS cells in the G1 phase of the cycle grown under pressure at 0 and 20 mmHg. These were gated to exhibit the cells in G1 phase which were presumably not in the dynamic phase of S and the transition into G2. They were smaller at 24 hours as indicated by the forward scatter profile and then became gradually larger at 48 and 72 hours. This was found to be statistically significant (p<0.01). Side scatter as a measure of granularity was similarly affected by pressure and this was statistically significant ($p<0.01$).

Figure 7B:
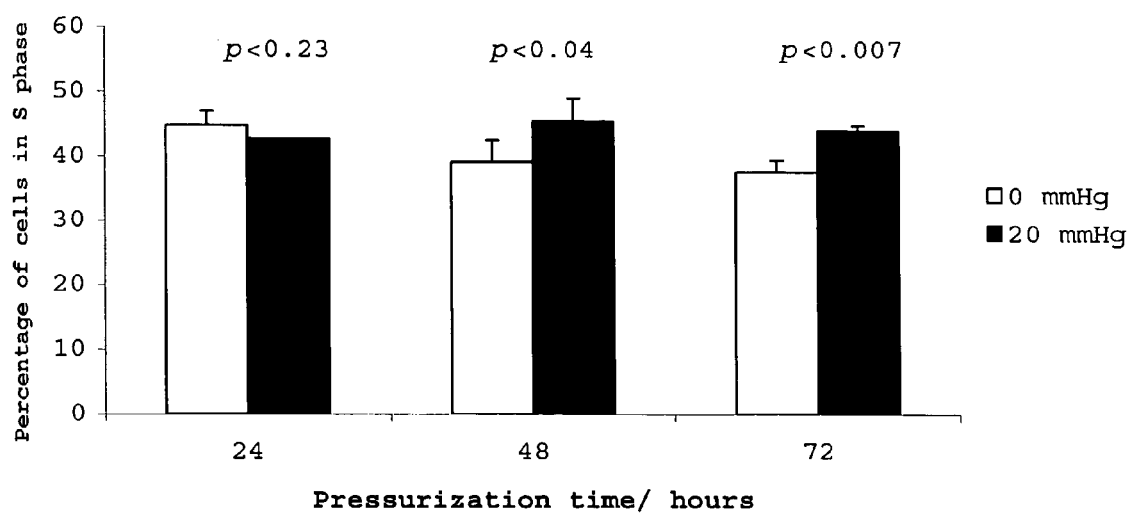

FIG. 7(a) shows the cell cycle analysis as determined by propidium iodide FL2-A fluorescence of HOS cells grown at two pressures. This showed that while the cells began at 24 hours with similar rates of proliferation as indicated by a similar proportion of cells in S phase, at 48 and 72 hours, the cells under pressure were at a higher proliferative state with a greater number of cells in S phase ($p<0.01$). FIG. 7(b) shows the percentage of cells in S phase at the three time points at two pressures. This shows the significant increase in cells in S phase at 48 and 72 hours as described above.

FIG. 9 shows the relationship of cell death under two pressures with time. There was an increasing amount of cell death in the pressurized chambers at 20 mmHg compared with the chambers at 0 mmHg over the three time points. This is postulated to account for the relatively modest increase in number of cells exhibited in FIG. 14a despite the cells having a greater proliferative phenotype shown in FIGS. 7a,b. These assessments however failed to achieve significance. This may be due to the general limitations of using the pre-G1 fraction as an assessment of death[24-27].

Figure 8B:
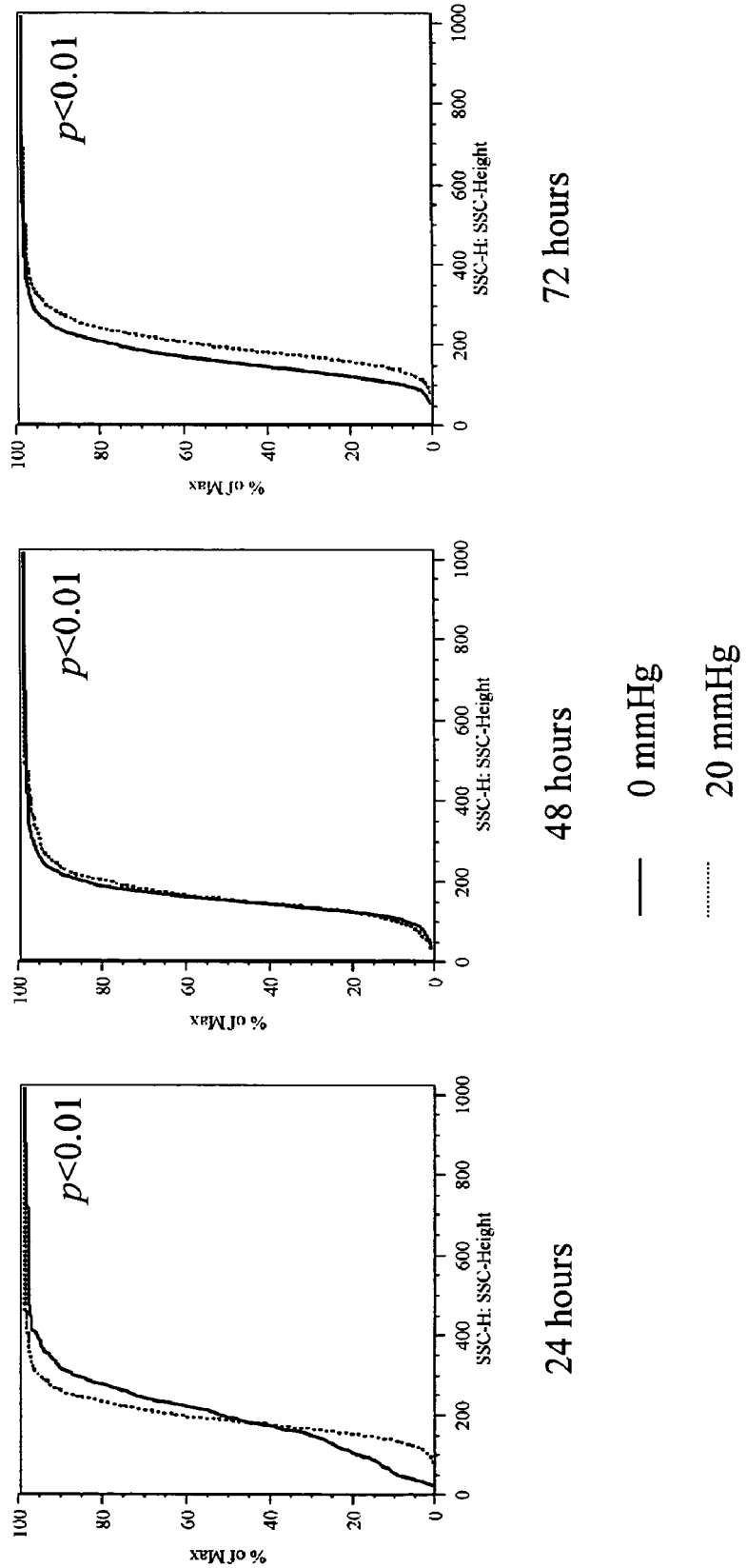

FIG. 10 shows the relative expression of E2F1 and E2F4 at 0 and 20 mmHg. Each data point represents the mean of six real time PCR results with error bars representing the standard error of the mean. It shows a statistically significant up-regulation of E2F-1($p<0.03$) and E2F-4($p<0.002$) under pressure. This may account for the greater fraction of cells in S phase as seen under pressure as described in FIG. 8.

FIGS. 14a-d shows the results of an apoptosis study for the HOS cell line. The data showed the absence of apoptosis in cells grown at atmospheric pressure (a) and under pressure at 20 mmHg (b). Apoptosis was reliably observed in the HL60 control (c). DNA gel electrophoresis did not show the presence of a 100 bp ladder characteristic of apoptosis (d). Using flow cytometry, no evidence of apoptosis as the mechanism of cell death were observed with the H1299 and MCF7 cell lines.

Experiment 5

Influence of Hydrostatic Pressure on Tumor Cell Chemosensitivity

Figure 14:
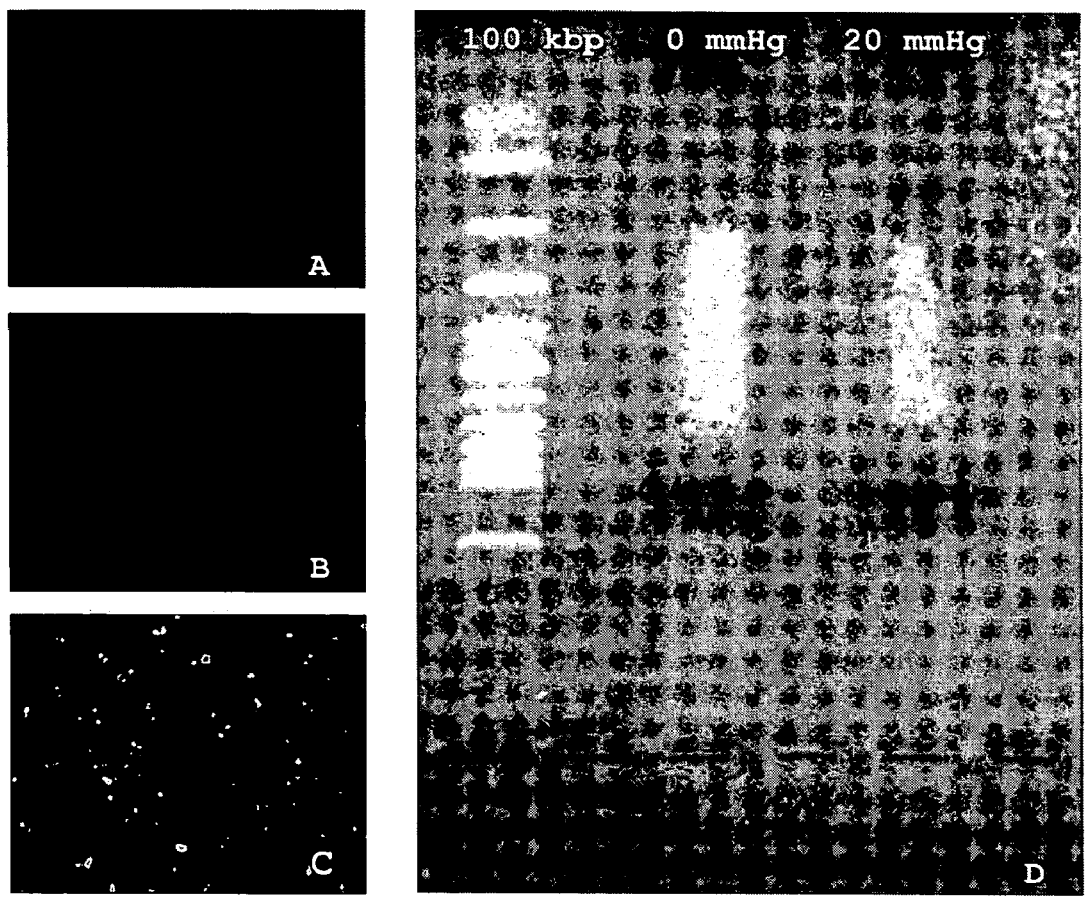

FIGS. 12a,b show the results of the doxorubicin and cisplatin chemosensitivity assays under conventional normal pressure conditions. While there is a statistically significant difference ($p<0.05$) in the ED50 between cells grown at atmospheric pressure and those grown under 20 mmHg of pressure, this difference is small. When this experiment was performed with cells grown under pressure on the membranes which were immediately cut and exposed to doxorubicin this difference became more pronounced (FIG. 13a,b). The cells grown under pressure and exposed to serial dilutions of cisplatin and doxorubicin showed marked differences in growth between the pressurized and non-pressurized systems at 0.16 and 1 µ/ml (FIG. 14).

Discussion

Our measurements of IFP in human OS confirmed the presence of elevated interstitial fluid pressure in this tumor. While the etiology of the elevated IFP in OS is similar to that in other solid tumors, the IFP measured is higher than observed in other soft tissue solid tumors (8, 9, 10, 11). Two reasons, related to the physiological distinction between OS and other solid tumors, may explain this difference. First, unlike normal soft tissues, except brain tissue, bone lacks a significant lymphatic system.

The excess interstitial fluid that forms within the OS tumor percolates outward towards the normal bone periphery. It accumulates within the interstitium but is not drained by a lymphatic system for return to the circulation as occurs in the normal tissues surrounding other solid tumors. Secondly, OS creates a rigid matrix, making it less compliant than all other solid tumors. Consequently, this tumor is less able to respond to its internal pressure by elastic expansion. The excess fluid that accumulates within the OS' interstitial spaces will result in higher IFP than that observed in soft tissue tumors because fluid percolation is slower and the tumor tissue will not expand to the same extent from the internal stresses. Elevated fluid pressure is one reason used to explain the pain associated with bony tumors (1).

The hydrostatic pressures that were used in the cell culture experiments 2-5 reflect the IFP range measured in human patients with osteosarcoma undergoing surgical biopsy and are similar to those reported by Chigira et al. In addition, canine osteosarcoma IFP has been reported to be in the same range, though is frequently higher (3) than human OS tumors.

Applicants observed that the presence of the HPA with the modified cassette does not interfere with cell population dynamics and that the trans-membrane gas exchange of the cells with the incubators' gas environment is unaffected. This latter point is indirectly inferred from the similarity in media pH at the end of the experiments; a hypoxic environment would have resulted in a more acidic growth media.

The pressurized cell culture system demonstrated that OS population dynamics were influenced by the media's fluid pressures. The elevated pressures may have induced a phenotypic change by selecting out those cells that could tolerate the applied pressure. For example, "pressure-acclimated" cells grew at a faster rate than un-pressurized cells. The data also indicates that elevated pressures can induce significant changes in population dynamics as pressures increase and suggests that there exists a "pressure threshold" that tumor cells can not tolerate and results in their death. The data suggest that actual value is cell-line dependent. While not examined in this study, the influence of the tumor matrix may compartmentalize the pressure and influence its effect.

Cell proliferation was further investigated using cell cytometry. The experiments suggest that after 48 hours of pressurization the cells adopt a more proliferative phenotype with more cells in S phase as compared to the non-pressurized cell population. This was further supported by forward scatter and side scatter characteristics that suggested that the cells were synthesizing cellular products in preparation of division and hence were bigger than their non-pressurized counterparts. Also, the finding that the E2F transcription factors were up-regulated suggests that pressure may induce the cells to undergo proliferation via a genetic mechanism. This phenomenon has been demonstrated in various non-neoplastic systems where genetic mechanisms have been postulated to work through a baroreceptor system which converges on the cell cycle[14,28]. This present data suggests that such a mechanism may exist in osteogenic sarcomas as well.

Cell death was also shown to be increased in these pressurized cell populations. This was higher than that seen in their non-pressurized counterparts. In this study the applicants used two methods of assessing cell death. Gating for cells in the pre-G1 fraction of the cell cycle analysis is an established index of cell death[25]. This provides an indication of cell death based on the amount of DNA debris within the system. The adherent properties of the cassette complicate this traditional system of assessment of cell death due to the difficulty in eliminating debris. Despite this limitation, the profile of the pre-G1 gated event frequencies in FIG. 9 suggest that while modest, the amount of death within the pressurized chambers was higher than the chambers at atmospheric pressure. The absence of evidence of apoptosis further suggests that the mechanism of cell death is necrosis. This has been similarly shown in other experiments which look at cell death under pressure[4]. This accounts for the finding that, in non-confluent cultures, cell number within the pressurized chambers did not greatly exceed the number within the non-pressurized chambers despite having a more proliferative phenotype. Whether this cell death is a function of the increased pressure per se or the increased competition for nutrients in these more proliferative cells is unclear. The implication of these findings is that cells grown under pressure are in a more dynamic state than those grown without pressure. It also indicates that the situation within the in vivo system may be more dynamic and less adequately represented by traditional culture systems.

The cell proliferation and cytometry findings formed the basis for the chemosensitivity study. Proliferative tumors are theoretically more sensitive to chemotherapy. Cell cycle active agents would interfere with processes leading to cell division and hence cells at a higher rate of division would be more profoundly affected. Cell cycle independent agents like cisplatin directly platinate DNA and hence affect most functions of the cell. These effects would therefore also be more pronounced in proliferative cell types where cell activity is increased.

In this study cells grown under pressure were more sensitive to chemotherapeutic agents as shown in FIGS. 11 and 12. Of interest, this effect was muted when cells were trypsinized, freed from excess pressure and allowed to reattach over a 24 hour period before being tested again as shown in FIG. 13. This suggests that this effect is a phenomenon that exists only while the cells remain pressurized as in the in vivo situation. The other implication is that tumors which experience elevated pressures in their in vivo state propagate as relatively resistant lines in cultures at atmospheric pressure. This may have some bearing on investigations involving pathways and mechanisms that influence the proliferative state of cells. The findings suggest that chemotherapy testing in conventional systems may not adequately reflect the in vivo situation.

Conclusions

Human OS was shown to have an elevated IFP that was significantly greater than that observed in other soft tissue solid tumors. The cell culture cassette-HPA assembly introduced herein is a useful and convenient system for applying the clinically relevant hydrostatic pressures observed within in vivo solid tumors to in vitro cell culture studies.

The experiments performed using this system determined that hydrostatic pressure applied to OS tumor cells affects their population dynamics in a cell line specific manner. It also raises the possibility of a mechano-transductive mechanism that affects cancer cell proliferation. The observation in the U2OS cells that pressurization at typical levels of tumor interstitial pressures induced population decline has major implications in the understanding of solid tumor physiology, genesis of necrosis, capillary density and therapeutic response to chemotherapy.

Advantages

The problem that the adapter invention solves is growing tumor cells within a cell culture cassette at elevated hydrostatic pressures in a one atmosphere gas environment. The high-pressure design can accomplish the same high-pressure cell culture functionality without the need for additional hardware facilitating closer packing within growth incubators.

Disadvantages or Limitations:

The membrane exposure to ambient gases is reduced by the size of the openings provided by the pressure adapter's or high pressure cassettes' screen mesh.

To summarize, this invention provides the cell culture cassette, consisting of a thin plastic case with two gas permeable membrane sides and two rubber infusion ports on the top of the cassette, with a means to expand its experimental functionality. The cassette has been successfully used for culturing a variety of single cell organisms under typical culture conditions. While it can be used to culture solid tumor cells, it is not suitable for simulating the in vivo growth conditions of solid tumor cells. These conditions typically include elevated and pulsatile interstitial pressures. When the cell culture cassette is filled with growth media and the media's internal pressure is raised to typical in vivo intra-tumoral pressures, the cassette's membrane walls bulge. The magnitude of the bulging is related to the applied pressure and elasticity of the membrane. This bulging result in interior fluid volume changes and the potential for membrane rupture. In addition, the infusion port is subject to leaking following media delivery through the rubber within the port. The high pressure adapter described within this invention permits the cell culture cassette to be used under pressurized media conditions without significant changes in its internal volume, eliminates infusion port leakage and provides support for valve assemblies to permit continual communication with the cell culture media for pressure maintenance, fluid sampling, etc. As an alternative, the applicants introduce a design for a high-pressure cell culture cassette that incorporates the functionality of the high-pressure adapter with a low-pressure cassette.

The five studies have shown that the incorporation of physiologic pressure as an additional factor in culture may result in significant changes to the cell under study. These findings suggest that pressure is a critical parameter that should be included in the design of cell culture systems that would better replicate the in vivo situation.

Pressurized Multi-Well Cell Culture Cluster

The prototype for a new device for growing tumor or other cells under hydrostatic pressure which can be useful for screening chemotherapy drugs is in progress. The "Pressurized Multi-Well Cell Culture Cluster", FIG. 15, provides certain advantages, i.e., the device can create single or multiple hydrostatic pressures in multiple wells. The imposed pressures are determined from pressurization plate designs. However, this device is more expensive to produce than the standard plates.

The device is composed of four components, shown in FIG. 15. The perforated bottom plate 71 is secured to the reaction block 72. Cells are placed into the growth chambers 73 containing standard growth media per usual cell culture technique. The pressurization lid 74 studded with slanted capping plugs 75 is positioned over the reaction block and carefully inserted to remove the gas over the media and simultaneously apply pressure. The magnitude of the pressure is dependent upon the length of the plugs. As shown in FIG. 15, two lengths are apparent. However, many combinations are possible. Further, the capping plugs can be height adjusted by screwing them into the pressurization lid to the desired depth: The assembly is clamped together and placed into an incubator. The entire assembly is made from clear plastic and analysis of chemotherapy effects are analyzed per usual methods. 76: membrane bottom; 77: O-ring; 78: groove for air release.

The design shown in FIG. 15 has eight (8) growth cylinders 73, however, it can be fabricated with as many as needed, for instance, 98, the number of wells in the unpressurized units.

What is claimed is:

1. A method of growing cells under static or variable pressure comprising steps of:
    a. obtaining an amount of cells;
    b. determining the interstitial fluid pressure range experienced by said cells under in vivo conditions;
    c. seeding said cells in a fluid growth media within an apparatus comprising (i) a cell culture cassette comprising a cassette frame; two side walls secured to each side of the cassette frame to form a cell growing chamber; and ports for adjusting fluid pressure or flow, for providing culture media or cell culture, or for sampling cell culture or culture media within the cell growing chamber; (ii) an adapter comprising two side assemblies with each side assembly comprising a frame with a rigid support that fits over the cell culture cassette, wherein said side assemblies are attached at one end and positioned over the two side walls of the cell culture cassette; and (iii) a means to secure the two side assemblies over the two side walls of the cell culture cassette;
    d. applying static or dynamic hydrodynamic pressure via the ports to the cell culture cassette within said interstitial fluid pressure range; and
    e. providing an amount of nutrient supply to the cell culture cassette to support cell growth or proliferation.

2. The method of claim 1, wherein the cells are tumor cells.

3. The method of claim 2, wherein the tumor is osteogenic sarcoma, osteosarcoma, adenocarcinoma, or non-small cell lung cancer.

4. The method of claim 1, wherein the apparatus is capable of sustaining a pressure selected from the group consisting of physiological pressure, pressure of up to 150 mmHg, and negative pressure.

5. The method of claim 1, wherein the cell culture cassette further comprises baffles that regulate the flow rate or flow profile of fluid through the cell culture cassette.

6. The method of claim 1, wherein the rigid support comprises a mesh.

7. The method of claim 6, wherein the mesh is made of a material selected from the group consisting of plastic, ceramic, stainless steel, platinum, gold, titanium, and biocompatible metal.

8. A method for identifying an agent capable of inhibiting tumor cell growth, comprising steps of:
    a. determining the interstitial fluid pressure range experienced by the tumor cells under in vivo conditions;
    b. contacting said agent with tumor cells grown under said interstitial fluid pressure range in an apparatus comprising (i) a cell culture cassette comprising a cassette frame; two side walls secured to each side of the cassette frame to form a cell growing chamber; and ports for adjusting fluid pressure or flow, for providing culture media or cell culture, or for sampling cell culture or culture media within the cell growing chamber; (ii) an adapter comprising two side assemblies with each side assembly comprising a frame with a rigid support that fits over the cell culture cassette, wherein said side assemblies are attached at one end and positioned over the two side walls of the cell culture cassette; and (iii) a means to secure the two side assemblies over the two side walls of the cell culture cassette; and
    c. examining the tumor cells to determine whether the growth of tumor cells is inhibited.

9. The method of claim 8, wherein the apparatus is capable of sustaining a pressure selected from the group consisting of physiological pressure, pressure of up to 150 mmHg, and negative pressure.

10. The method of claim 8, wherein the cell culture cassette further comprises baffles that regulate the flow rate or flow profile of fluid through the cell culture cassette.

11. The method of claim 8, wherein the rigid support comprises a mesh.

12. The method of claim 11, wherein the mesh is made of a material selected from the group consisting of plastic, ceramic, stainless steel, platinum, gold, titanium, and biocompatible metal.

13. A method for determining effective amount of an agent capable of inhibiting tumor cell growth comprising steps of:
    a. determining the interstitial fluid pressure range experienced by the tumor cells under in vivo conditions;
    b. contacting said agent at different amounts with tumor cells grown under said interstitial fluid pressure range in an apparatus comprising (i) a cell culture cassette comprising a cassette frame; two side walls secured to each side of the cassette frame to form a cell growing chamber; and ports for adjusting fluid pressure or flow, for providing culture media or cell culture, or for sampling cell culture or culture media within the cell growing chamber; (ii) an adapter comprising two side assemblies with each side assembly comprising a frame with a rigid support that fits over the cell culture cassette, wherein said side assemblies are attached at one end and positioned over the two side walls of the cell culture cassette; and (iii) a means to secure the two side assemblies over the two side walls of the cell culture cassette;
    c. examining the tumor cells to determine whether the growth of tumor cells is inhibited; and
    d. determining the effective amount of the agent which causes tumor cell inhibition.

14. The method of claim 13, wherein the apparatus is capable of sustaining a pressure selected from the group consisting of physiological pressure, pressure of up to 150 mmHg, and negative pressure.

15. The method of claim 13, wherein the cell culture cassette further comprises baffles that regulate the flow rate or flow profile of fluid through the cell culture cassette.

16. The method of claim 13, wherein the rigid support comprises a mesh.

17. The method of claim 16, wherein the mesh is made of a material selected from the group consisting of plastic, ceramic, stainless steel, platinum, gold, titanium, and biocompatible metal.

* * * * *

UNITED STATES PATENT AND TRADEMARK OFFICE
CERTIFICATE OF CORRECTION

| | | |
|---|---|---|
| PATENT NO. | : 7,435,587 B2 | Page 1 of 1 |
| APPLICATION NO. | : 11/018094 | |
| DATED | : October 14, 2008 | |
| INVENTOR(S) | : Gene R. Diresta, John H. Healey and Robert Schwar | |

It is certified that error appears in the above-identified patent and that said Letters Patent is hereby corrected as shown below:

Please replace the paragraph that begins on Col. 1, line 8 as follows:

-- This application was supported in part by a National Cancer Institute Core Grant No. 08748. Accordingly, the United States Government has certain rights in this invention. --

Signed and Sealed this

Fifth Day of May, 2009

JOHN DOLL
*Acting Director of the United States Patent and Trademark Office*